United States Patent
Wan et al.

(10) Patent No.: US 12,234,233 B2
(45) Date of Patent: Feb. 25, 2025

(54) CRYSTAL FORM OF PHOSPHODIESTERASE INHIBITOR, PREPARATION METHOD THEREFOR AND USE THEREOF

(71) Applicant: TRANSTHERA SCIENCES (NANJING), INC., Jiangsu (CN)

(72) Inventors: Zhonghui Wan, Jiangsu (CN); Lin Li, Jiangsu (CN)

(73) Assignee: TRANSTHERA SCIENCES (NANJING), INC., Jiangsu (CN)

( * ) Notice: Subject to any disclaimer, the term of this patent is extended or adjusted under 35 U.S.C. 154(b) by 676 days.

(21) Appl. No.: 17/439,591

(22) PCT Filed: Mar. 13, 2020

(86) PCT No.: PCT/CN2020/079337
§ 371 (c)(1),
(2) Date: Sep. 15, 2021

(87) PCT Pub. No.: WO2020/187165
PCT Pub. Date: Sep. 24, 2020

(65) Prior Publication Data
US 2022/0194934 A1    Jun. 23, 2022
US 2023/0125064 A2    Apr. 20, 2023

(30) Foreign Application Priority Data

Mar. 15, 2019   (CN) .......................... 201910199611.6
Mar. 25, 2019   (CN) .......................... 201910228418.0
Aug. 26, 2019   (CN) .......................... 201910789020.4

(51) Int. Cl.
C07D 471/04   (2006.01)
(52) U.S. Cl.
CPC ........ *C07D 471/04* (2013.01); *C07B 2200/13* (2013.01)
(58) Field of Classification Search
CPC .. C07D 471/04; C07B 2200/13; A61K 45/06; A61K 31/4545; A61P 9/04; A61P 9/10; A61P 25/00; A61P 25/18; A61P 25/28; A61P 3/00; A61P 3/04; A61P 3/10; A61P 7/00; A61P 7/06
See application file for complete search history.

(56) References Cited

U.S. PATENT DOCUMENTS

| 9,133,164 B2 | 9/2015 | Gaweco et al. |
| 2007/0270395 A1 | 11/2007 | Sircar et al. |
| 2020/0115384 A1 | 4/2020 | Wu et al. |
| 2021/0130366 A1* | 5/2021 | Wu .......................... A61P 25/28 |

FOREIGN PATENT DOCUMENTS

| CN | 1382141 A | 11/2002 |
| EP | 1225173 A1 | 7/2002 |
| EP | 3689876 A1 | 8/2020 |
| EP | 3915992 A1 | 1/2021 |
| WO | 2017019723 A1 | 2/2017 |
| WO | 2017019724 A1 | 2/2017 |
| WO | 2017019726 A1 | 2/2017 |
| WO | 2019062733 A1 | 4/2019 |

OTHER PUBLICATIONS

Oxford English Dictionary, "to prevent" (accessed Apr. 25, 2024) (Year: 2024).*
Singh, N.; Patra, S. "Phosphodiesterase 9: Insights from protein structure and role in therapeutics" 2014, Life Sciences, vol. 106, pp. 1-11. (Year: 2014).*
Minnesota Evidence-based Practice Center, "Interventions to Prevent Age-Related Cognitive Decline, Mild Cognitive Impairment, and Clinical Alzheimer's-Type Dementia" Mar. 2017, U.S. Department of Health and Human Services' Agency for Healthcare Research and Quality. (Year: 2017).*
Mayo Clinic, "Mild Cognitive Impairment", website updated Jul. 28, 2018, accessed via Wayback Machine Apr. 25, 2024. (Year: 2018).*
Lopez, O. L. "Mild Cognitive Impairment" 2013, Continuum, vol. 19, pp. 411-424. (Year: 2013).*
Shafiee-Nick, R.; et al. "A comprehensive review on the potential therapeutic benefits of phosphodiesterase inhibitors on cardiovascular diseases" 2017, Biomedicine and Pharmacotherapy, vol. 94, p. 541-556. (Year: 2017).*
Huang, X.- F.; et al. "A novel PDE9 inhibitor WYQ-C36D ameliorates corticosterone-induced neurotoxicity and depression-like" 2018, CNS Neuroscience and Therapeutics, vol. 24, pp. 889-896. (Year: 2018).*
Notification on Violation of Invention Unity Requirement dated Feb. 13, 2023, directed to Russian Patent Application No. 2021129952; 25 pages.

(Continued)

*Primary Examiner* — Eric Olson
*Assistant Examiner* — Benjamin M Brandsen
(74) *Attorney, Agent, or Firm* — Venable LLP; Michele V. Frank

(57) ABSTRACT

The present invention falls within the technical field of medicine, and in particular relates to a crystal form of a phosphodiesterase inhibitor as shown in formula (I), a preparation method therefor and the use thereof.

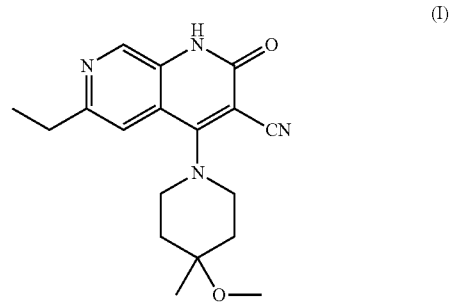

(I)

19 Claims, 18 Drawing Sheets

(56) References Cited

OTHER PUBLICATIONS

Examination Report under Sections 12 & 13 of the Patents Act, 1970 and the Patents Rules, 2003, mailed Apr. 1, 2022, directed to Indian Application No. 2021147044255; 6 pages.
Supplementary European Search Report for EP Application No. 20774770 dated Nov. 28, 2022.
Official Communication from SG Application No. 11202110055S dated Dec. 26, 2022.
International Search Report with English Translation and Written Opinion in corresponding International Application No. PCT/CN2020/079337 mailed May 27, 2020 (8 pages).

* cited by examiner

CRYSTAL FORM OF PHOSPHODIESTERASE INHIBITOR, PREPARATION METHOD THEREFOR AND USE THEREOF

This application is a National Stage Application under 35 U.S.C. § 371 PCT/CN2020/079337, filed Mar. 13, 2020, which claims priority benefit from Chinese Patent Application No. 201910199611.6, filed on Mar. 15, 2019, Chinese Patent Application No. 201910228418.0, filed Mar. 25, 2019, and Chinese Patent Application No. 201910789020.4, filed Aug. 26, 2019 the entire content of which is incorporated herein by reference. All references cited anywhere in this specification, including the Background and Detailed Description sections, are incorporated by reference as if each had been individually incorporated.

TECHNICAL FIELD

The present invention falls within the technical field of medicine, and in particular relates to a crystal form of a phosphodiesterase inhibitor, a preparation method therefor and the use thereof.

BACKGROUND ART

Phosphodiesterase 9 is an important member of the PDE family and has a very high selectivity for cGMP. Phosphodiesterase 9 inhibitors can be used to treat diseases with respect to cognitive impairment caused by central nervous system disorders, such as Alzheimer's disease and schizophrenia, and neurodegenerative disease of brain.

In the process of drug development, the study on crystal forms is very important, and the crystal forms of a compound are quite different from other forms thereof in terms of stability, solubility, etc. The present inventors have conducted researches on PDE9 inhibitor compounds in order to obtain pharmaceutically acceptable crystal forms.

SUMMARY OF THE INVENTION

An object of the present invention is to provide a crystal form of a compound of formula (I) and a preparation method therefor.

The present invention provides a crystal form I of a compound as shown in formula (I):

the crystal form I of a compound as shown in formula (I), 6-ethyl-4-(4-methoxy-4-methylpiperidin-1-yl)-2-oxo-1,2-dihydro-1,7-diazanaphthal ene-3-carbonitrile, has an X-ray powder diffraction pattern comprising characteristic peaks at 7.3±0.2, 13.6±0.2, 14.5±0.2°, 18.0±0.2°, 19.1±0.2, 22.0±0.2° and 23.4±0.2° 2θ, as determined by using Cu-Kα radiation,

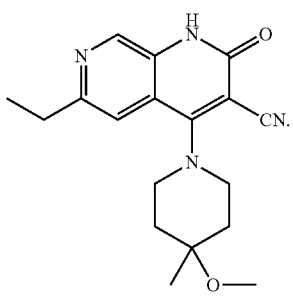

(I)

In an embodiment of the present invention, in addition to the characteristic peaks mentioned above, the X-ray powder diffraction pattern of the crystal form I of the compound as shown in formula (I) comprises characteristic peaks at 14.2±0.2, 16.1±0.2°, 19.4±0.2° and 25.6±0.2° 2θ, as determined by using Cu-Kα radiation.

In an embodiment of the present invention, in addition to the characteristic peaks mentioned above, the X-ray powder diffraction pattern of the crystal form I of the compound as shown in formula (I) comprises characteristic peaks at 15.1±0.2° and 17.6±0.2° 2θ, as determined by using Cu-Kα radiation.

In an embodiment of the present invention, the crystal form I of the compound as shown in formula (I) exhibits an X-ray powder diffraction pattern as substantially depicted in FIG. 1 when Cu-Kα radiation is used.

The present invention further provides a method for preparing the crystal form I of the compound as shown in formula (I):

the method comprises dissolving the compound of formula (I) in a single or mixed solvent, raising the temperature to reflux until complete dissolution, and slowly decreasing the temperature until the crystal form I is precipitated.

In an embodiment of the present invention, the single or mixed solvent is selected from: one of or a mixture of methanol, ethanol, isopropanol, toluene, acetone, tetrahydrofuran, dichloromethane, dichloroethane, ethyl acetate, acetonitrile, methyl tert-butyl ether, 2-methyltetrahydrofuran, dimethyl sulfoxide and water.

In an embodiment of the present invention, the single or mixed solvent is selected from: methanol, ethanol, isopropanol, toluene, acetone, tetrahydrofuran, water\ethanol, water\isopropanol, dichloromethane, ethyl acetate and acetonitrile.

In an embodiment of the present invention, the expression "decreasing the temperature" refers to decreasing the temperature to less than 30° C., preferably to room temperature. The expression "room temperature" refers to 15° C.-25° C., or refers to 10° C.-30° C. based on Pharmacopoeia of the People's Republic of China.

In an embodiment of the present invention, the single or mixed solvent is used in an amount of 20-30 times the volume of the compound of formula (I).

The present invention further provides another method for preparing the crystal form I of the compound as shown in formula (I):

the method comprises completely dissolving the compound of formula (I) in a single or mixed solvent, and volatilizing the single or mixed solvent until the system is saturated and the crystal form I is precipitated.

In an embodiment of the present invention, the single or mixed solvent is selected from: one of or a mixture of methanol, ethanol, isopropanol, toluene, acetone, tetrahydrofuran, dichloromethane, dichloroethane, ethyl acetate, acetonitrile, methyl tert-butyl ether, 2-methyltetrahydrofuran, dimethyl sulfoxide and water.

In an embodiment of the present invention, the single or mixed solvent is selected from: methanol, ethanol, isopropanol, toluene, acetone, tetrahydrofuran, water\ethanol, water\isopropanol, dichloromethane, ethyl acetate, acetonitrile, dichloromethane\acetone, dichloromethane\acetonitrile, dichloromethane\ethyl acetate, dichloromethane\methyl tert-butyl ether, dichloromethane\tetrahydrofuran, dichloromethane\ethanol, dichloromethane\isopropanol, dichloromethane\toluene, dichloromethane\water\ethanol, and dichloromethane\water\isopropanol.

In an embodiment of the present invention, the single solvent is selected from methanol, ethanol, isopropanol, toluene, acetone, tetrahydrofuran, dichloromethane, ethyl acetate and acetonitrile.

In an embodiment of the present invention, the mixed solvent is selected from a mixture of dichloromethane and acetone, acetonitrile, ethyl acetate, methyl tert-butyl ether, tetrahydrofuran, ethanol, isopropanol, toluene, water\ethanol and water\isopropanol, with a volume ratio of 1:0.5-3, preferably 1:1.5-3.

In an embodiment of the present invention, the single or mixed solvent is used in an amount of more than 30 times the volume of the compound of formula (I).

In an embodiment of the present invention, the expression "volatilizing" may refer to natural volatilization, or volatilization promoted by heating to a certain temperature.

The present invention provides a crystal form II of a hydrochloride of a compound as shown in formula (I):

the crystal form II of a hydrochloride of a compound as shown in formula (I), 6-ethyl-4-(4-methoxy-4-methylpiperidin-1-yl)-2-oxo-1,2-dihydro-1,7-diazanaphthal ene-3-carbonitrile, has an X-ray powder diffraction pattern comprising characteristic peaks at 4.0±0.2, 6.7±0.2, 7.9±0.2°, 13.5±0.2°, 14.2±0.2, 15.4±0.2°, 20.2±0.2° and 22.0±0.2° 2θ, as determined by using Cu-Kα radiation.

In an embodiment of the present invention, in addition to the characteristic peaks mentioned above, the X-ray powder diffraction pattern of the crystal form II of the compound as shown in formula (I) comprises characteristic peaks at 10.2±0.2°, 13.8±0.2, 14.6±0.2°, 26.40±0.2° and 26.80±0.2° 2θ, as determined by using Cu-Kα radiation.

In an embodiment of the present invention, the crystal form II of the compound as shown in formula (I) exhibits an X-ray powder diffraction pattern as substantially depicted in FIG. 6 when Cu-Kα radiation is used.

The present invention further provides a method for preparing the crystal form II of the compound as shown in formula (I):

the method comprises adding a single or mixed solvent to the hydrochloride of the compound of formula (I), heating the mixture until complete dissolution, and slowly cooling down the heated mixture until the crystal form II is precipitated;

In an embodiment of the present invention, the single or mixed solvent is selected from: one of or a mixture of methanol, ethanol, isopropanol and water; preferably, the single or mixed solvent is selected from methanol, ethanol, isopropanol, water\methanol, water\ethanol, and water\isopropanol.

In an embodiment of the present invention, the expression "cooling down" refers to cooling down to room temperature. The expression "room temperature" refers to 15° C.-25° C., or refers to 10° C.-30° C. based on Pharmacopoeia of the People's Republic of China.

The present invention provides a crystal form III of a hydrochloride of a compound as shown in formula (I):

the crystal form III of a hydrochloride of a compound as shown in formula (I), 6-ethyl-4-(4-methoxy-4-methylpiperidin-1-yl)-2-oxo-1,2-dihydro-1,7-diazanaphthal ene-3-carbonitrile, has an X-ray powder diffraction pattern comprising characteristic peaks at 5.2±0.2, 6.4±0.2, 15.3±0.2°, 18.6±0.2°, 22.0±0.2° and 26.4±0.2° 2θ, as determined by using Cu-Kα radiation.

In an embodiment of the present invention, in addition to the characteristic peaks mentioned above, the X-ray powder diffraction pattern of the crystal form III of the compound as shown in formula (I) comprises characteristic peaks at 8.0±0.2°, 10.3±0.2°, 13.5±0.2° and 25.0±0.2° 2θ, as determined by using Cu-Kα radiation.

In an embodiment of the present invention, the crystal form III of the compound as shown in formula (I) exhibits an X-ray powder diffraction pattern as substantially depicted in FIG. 9 when Cu-Kα radiation is used.

The present invention further provides a method for preparing the crystal form III of the compound as shown in formula (I):

the method comprises adding a single or mixed solvent to the hydrochloride of the compound of formula (I), heating the mixture until complete dissolution, performing filtration while hot, and concentrating the filtrate until the crystal form III is precipitated.

In an embodiment of the present invention, the single or mixed solvent is selected from: one of or a mixture of acetonitrile, acetone, tetrahydrofuran and ethyl acetate.

The present invention provides a crystal form IV of a p-toluenesulfonate of a compound as shown in formula (I):

the crystal form IV of a p-toluenesulfonate of a compound as shown in formula (I), 6-ethyl-4-(4-methoxy-4-methylpiperidin-1-yl)-2-oxo-1,2-dihydro-1,7-diazanaphthal ene-3-carbonitrile, has an X-ray powder diffraction pattern comprising characteristic peaks at 5.8±0.2, 7.8±0.2, 9.3±0.2°, 11.3±0.2°, 13.7±0.2, 14.8±0.2° and 15.7±0.2° 2θ, as determined by using Cu-Kα radiation,

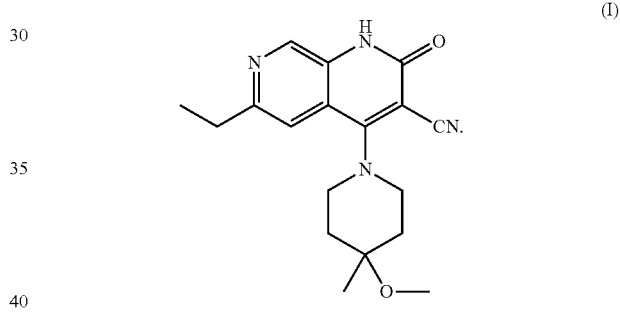

(I)

In an embodiment of the present invention, in addition to the characteristic peaks mentioned above, the X-ray powder diffraction pattern of the crystal form IV of the compound as shown in formula (I) comprises characteristic peaks at 17.1±0.2°, 18.7±0.2°, 20.0±0.2° and 22.4±0.2° 2θ, as determined by using Cu-Kα radiation.

In an embodiment of the present invention, the crystal form IV of the compound as shown in formula (I) exhibits an X-ray powder diffraction pattern as substantially depicted in FIG. 12 when Cu-Kα radiation is used.

The present invention further provides a method for preparing the crystal form IV of the compound as shown in formula (I):

the method comprises adding the compound of formula (I) to p-toluenesulfonic acid, heating the mixture until complete dissolution, and slowly decreasing the temperature until the crystal form IV is precipitated.

In an embodiment of the present invention, the expression "decreasing the temperature" refers to decreasing the temperature to less than 30° C., preferably to room temperature. The expression "room temperature" preferably refers to 15° C.-25° C., or 10° C.-30° C. based on Pharmacopoeia of the People's Republic of China.

In an embodiment of the present invention, the p-toluenesulfonic acid is used in an amount of 5-30 times the volume of the compound of formula (I).

In an embodiment of the present invention, the p-toluenesulfonic acid may be p-toluenesulfonic acid with different concentrations, or an aqueous solution of p-toluenesulfonic acid.

The present invention provides a crystal form V of a methanesulfonate of a compound as shown in formula (I):

the crystal form V of a methanesulfonate of a compound as shown in formula (I), 6-ethyl-4-(4-methoxy-4-methylpiperidin-1-yl)-2-oxo-1,2-dihydro-1,7-diazanaphthal ene-3-carbonitrile, has an X-ray powder diffraction pattern comprising characteristic peaks at 7.0±0.2, 9.7±0.2, 13.2±0.2°, 18.1±0.2°, 19.5±0.2, 20.7±0.2° and 21.7±0.2° 2θ, as determined by using Cu-Kα radiation.

In an embodiment of the present invention, in addition to the characteristic peaks mentioned above, the X-ray powder diffraction pattern of the crystal form V of the compound as shown in formula (I) comprises characteristic peaks at 16.9±0.2°, 18.6±0.2°, 19.1±0.2°, 20.2±0.2° and 28.0±0.2° 2θ, as determined by using Cu-Kα radiation.

In an embodiment of the present invention, the crystal form V of the compound as shown in formula (I) exhibits an X-ray powder diffraction pattern as substantially depicted in FIG. 13 when Cu-Kα radiation is used.

The present invention further provides a method for preparing the crystal form V of the compound as shown in formula (I):

the method comprises adding the compound of formula (I) to methanesulfonic acid, heating the mixture until complete dissolution, and then adding a solvent, subjecting the mixture to suction filtration, and drying the suction-filtered mixture to obtain V, wherein the solvent is methanol, ethanol or isopropanol.

In an embodiment of the present invention, the methanesulfonic acid is used in an amount of 5-30 times the volume of the compound of formula (I).

In an embodiment of the present invention, the methanesulfonic acid may be methanesulfonic acid with different concentrations, or an aqueous solution of methanesulfonic acid.

The present invention provides a crystal form VI of a sulfate of a compound as shown in formula (I):

the crystal form VI of a sulfate of a compound as shown in formula (I), 6-ethyl-4-(4-methoxy-4-methylpiperidin-1-yl)-2-oxo-1,2-dihydro-1,7-diazanaphthal ene-3-carbonitrile, has an X-ray powder diffraction pattern comprising characteristic peaks at 4.4±0.2, 7.1±0.2, 8.8±0.2°, 14.3±0.2°, 17.8±0.2, 19.6±0.2° and 21.6±0.2° 2θ, as determined by using Cu-Kα radiation, In an embodiment of the present invention, in addition to the characteristic peaks mentioned above, the X-ray powder diffraction pattern of the crystal form VI of the compound as shown in formula (I) comprises characteristic peaks at 25.5±0.2° and 27.7±0.2 2θ, as determined by using Cu-Kα radiation.

In an embodiment of the present invention, the crystal form VI of the compound as shown in formula (I) exhibits an X-ray powder diffraction pattern as substantially depicted in FIG. 14 when Cu-Kα radiation is used.

The present invention further provides a method for preparing the crystal form VI of the compound as shown in formula (I):

the method comprises adding the compound of formula (I) to an aqueous solution of sulfuric acid, heating the mixture until complete dissolution, and slowly decreasing the temperature until the crystal form VI of the sulfate of the compound of formula (I) is precipitated; or adding the sulfate of the compound of formula (I) to a single or mixed solvent, heating the mixture until complete dissolution, and slowly decreasing the temperature until the crystal form VI is precipitated.

In an embodiment of the present invention, the expression "decreasing the temperature" refers to decreasing the temperature to less than 30° C., preferably to room temperature. The expression "room temperature" refers to 10° C.-30° C., preferably 15° C.-25° C.

In an embodiment of the present invention, the aqueous solution of sulfuric acid is used in an amount of 2-30 times, preferably 2-10 times, more preferably 4 times, 5 times and 6 times the volume of the compound of formula (I).

In an embodiment of the present invention, the single or mixed solvent is used in an amount of 5-60 times, preferably 5-50 times, more preferably 10 times, 15 times and 50 times the volume of the sulfate of the compound of formula (I).

In an embodiment of the present invention, the single or mixed solvent is selected from one of or a mixture of acetone, ethanol, methanol and tetrahydrofuran; preferably, the solvent is a single solvent; more preferably, the single solvent is selected from acetone, ethanol, methanol and tetrahydrofuran.

The present invention provides a crystal form VII of a sulfate of a compound as shown in formula (I):

the crystal form VII of a sulfate of the compound as shown in formula (I), 6-ethyl-4-(4-methoxy-4-methylpiperidin-1-yl)-2-oxo-1,2-dihydro-1,7-diazanaphthal ene-3-carbonitrile, is characterized by having an X-ray powder diffraction pattern comprising characteristic peaks at 7.1±0.2, 13.6±0.2°, 14.5±0.2°, 18.0±0.2, 19.0±0.2°, 22.0±0.2° and 23.4±0.2° 2θ, as determined by using Cu-Kα radiation,

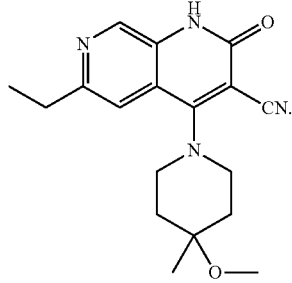

(I)

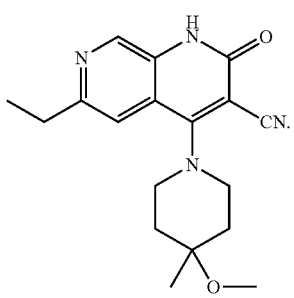

(I)

In an embodiment of the present invention, in addition to the characteristic peaks mentioned above, the X-ray powder diffraction pattern of the crystal form VII of the compound as shown in formula (I) comprises characteristic peaks at 15.0±0.2°, 16.1±0.2°, 17.4±0.2° and 19.4±0.2° 2θ, as determined by using Cu-Kα radiation.

In an embodiment of the present invention, the crystal form VII of the compound as shown in formula (I) exhibits an X-ray powder diffraction pattern as substantially depicted in FIG. 18 when Cu-Kα radiation is used.

The present invention further provides a method for preparing the crystal form VII of the compound as shown in formula (I):

the method comprises adding the sulfate of the compound of formula (I) to isopropanol, heating the mixture until complete dissolution, and slowly decreasing the temperature until the crystal form VII is precipitated.

In an embodiment of the present invention, the expression "decreasing the temperature" refers to decreasing the temperature to less than 30° C., preferably to room temperature. The expression "room temperature" refers to 10° C.-30° C., preferably 15° C.-25° C.

In an embodiment of the present invention, the isopropanol is used in an amount of 5-60 times, preferably 10-50 times, more preferably 30-50 times the volume of the crystal form VI. The present invention further provides a pharmaceutical composition comprising the crystal form I, II, III, IV, V, VI or VII of the compound as shown in formula (I), and one or more second therapeutically active agents.

The present invention further provides a pharmaceutical preparation comprising the crystal form I, II, III, IV, V, VI or VII of the compound as shown in formula (I).

In an embodiment of the present invention, the pharmaceutical preparation may comprise one or more pharmaceutical carriers.

The pharmaceutical carrier of the present invention may be one or more solid or liquid fillers suitable for human use. The pharmaceutical carrier preferably has sufficient purity and sufficiently low toxicity, and is compatible with the compound provided by the present invention without significantly reducing its efficacy. For example, the pharmaceutical carrier may be a filler, a binder, a disintegrant, a lubricant, an aqueous solvent, a non-aqueous solvent, etc.

The pharmaceutical preparation of the present invention can be made into any pharmaceutically acceptable dosage form, and a "therapeutically effective amount" of the crystal form I, II, III, IV, V, VI or VII of the compound of formula (I) as described above is administered in any suitable manner, such as orally, parenterally, rectally or pulmonarily, to a patient or subject in need of such treatment. When used for oral administration, the pharmaceutical preparation can be prepared into a tablet, a capsule, a pill, a granule, etc. When used for parenteral administration, the pharmaceutical preparation can be prepared into an injection, a sterile powder for injection, etc.

The present invention further provides the use of the crystal form I, II, III, IV, V, VI or VII of the compound as shown in formula (I), or the pharmaceutical preparation or pharmaceutical composition comprising the crystal form I, II, III, IV, V, VI or VII in the manufacture of a medicament for treating or preventing PDE9-mediated diseases. Specifically, the PDE9-mediated diseases comprise CNS diseases, and more specifically, comprise impairments associated with perception, attention, memory and learning, senile dementia, schizophrenia, age-related memory loss, vascular dementia, craniocerebral injury, stroke, post-stroke dementia, post-traumatic dementia, general attention deficit, attention deficit with learning and memory problems in children, Alzheimer's disease, Lewy body dementia, frontotemporal lobe degeneration dementia, cortical basal ganglionic degeneration dementia, amyotrophic lateral sclerosis disease, Huntington's disease, multiple sclerosis, thalamic degeneration, dementia in Creutzfeldt-Jakob disease, HIV dementia, schizophrenia, epilepsy, Korsakoff's psychosis, depression, bipolar affective disorder, etc. Specifically, the PDE9-mediated diseases comprise CNS-related diseases, and more specifically, comprise sleep disorder, metabolic syndrome, obesity, diabetes, hyperglycemia, dyslipidemia, impaired glucose tolerance, etc. Specifically, the PDE9-mediated diseases comprise heart diseases and blood diseases, and more specifically, comprise heart failure, anemia, sickle-cell disease, etc.

The present invention further provides the use of the crystal form I, II, III, IV, V, VI or VII of the compound as shown in formula (I), or the pharmaceutical preparation or the pharmaceutical composition comprising the crystal form I, II, IV, V, VI or VII in the treatment or prevention of PDE9-mediated diseases.

The present invention further provides a method for treating or preventing PDE9-mediated diseases, the method comprising administering to a patient in need thereof a therapeutically effective amount of the crystal form I, II, III, IV, V, VI or VII of the formula (I) as described above, or the pharmaceutical preparation or pharmaceutical composition comprising the crystal form I, II, III, IV, V, VI or VII.

DETAILED DESCRIPTION OF THE INVENTION

The expression "room temperature" in the present invention refers to the indoor temperature, which is usually 15° C.-25° C., or refers to 10° C.-30° C. based on Pharmacopoeia of the People's Republic of China.

The expression "times the volume" in the present invention refers to the volume (ml) of a solvent required to dissolve 1 g of a substance; for example, if the volume of the solvent required to dissolve 1 g of the compound of formula (I) is 20 ml, it is called 20 times the volume.

The expression "therapeutically effective amount" in the present invention refers to the amount of the aforementioned compound or the pharmaceutically acceptable salt and stereoisomer thereof, the composition or the pharmaceutical preparation that, when administered to a patient, can at least alleviate the symptoms of the patient's condition. The actual amount comprising the "therapeutically effective amount" will vary according to various situations, including but not limited to the specific conditions being treated, the severity of the condition, the physical and health status of the patient, and the administration route. An appropriate amount can be readily determined by a skilled medical practitioner using methods known in the medical field.

Excellent Effect of the Present Invention

It is found based on the research of the present invention that the crystal forms of the present invention have excellent physicochemical properties and pharmaceutical stability, and also have a greater improvement in pharmacodynamic and pharmacokinetic properties, which are more conducive to the research on druggability.

DETAILED DESCRIPTION OF EMBODIMENTS

Figure 1:
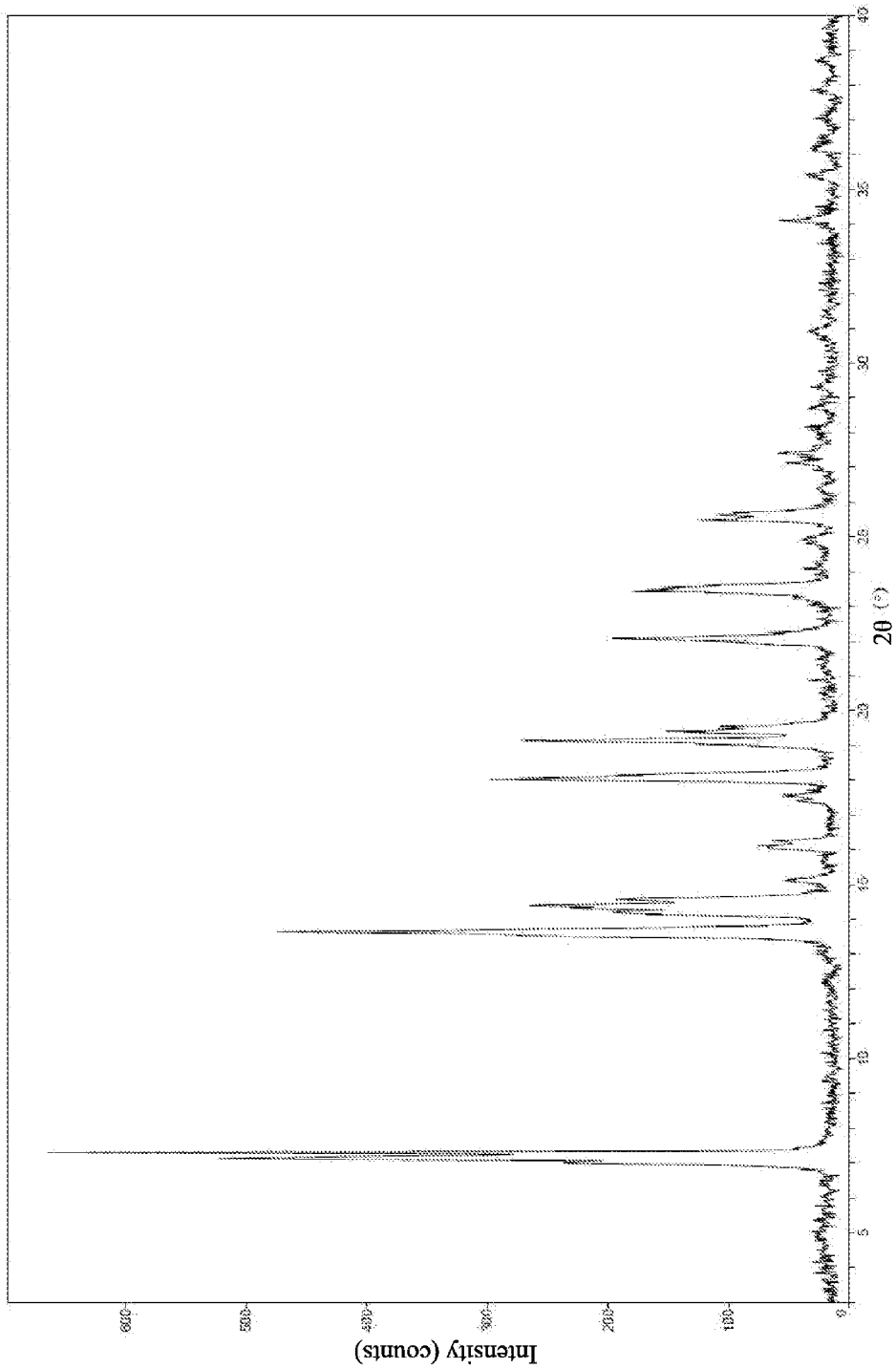
FIG. 1 is an X-ray powder diffraction (XRPD) pattern of the crystal form I of the compound of formula (I).

The above-mentioned content of the present invention will be further described in detail by way of particular examples, but this should not be construed as limiting the scope of the above-mentioned subject matter of the present invention to the following examples. All techniques achieved based on the above-mentioned content of the present invention fall within the scope of the present invention.

The abbreviations used herein are as follows:
"DIPEA" means N,N-diisopropylethylamine;
"RH" means relative humidity;
"DMF" means N,N-dimethylformamide;
"DCM" means dichloromethane;
"DMSO" means dimethyl sulfoxide.

Preparative Example 1: Synthesis of Intermediate 4,6-dichloro-2-oxo-1,2-dihydro-1,7-diazanaphthalene-3-carbonitrile Step 1: Synthesis of 6-chloro-2H-pyrido[3,4-d][1,3]oxazin-2,4(1H)-dione

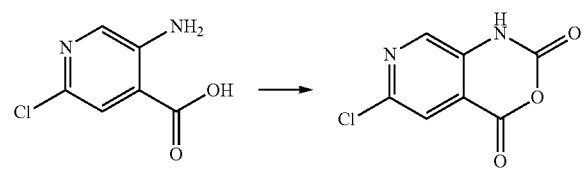 [SMILES: Nc1cnc(Cl)cc1C(=O)O ; O=c1[nH]c2cnc(Cl)cc2c(=O)o1]

5-amino-2-chloroisonicotinic acid (30 g, 0.1738 mol, 1.0 eq) was dissolved in N,N-dimethylformamide (300 mL), and N,N'-carbonyldiimidazole (48 g, 0.2955 mol, 1.7 eq) was added batchwise at 0° C.; and the mixture was slowly warmed to room temperature overnight. LC-MS showed that the reaction was completed, cooled to room temperature and is directly used for the next step without treatment.

Step 2: Synthesis of 6-chloro-4-hydroxyl-2-oxo-1,2-dihydro-1,7-diazanaphthalene-3-carbonitrile

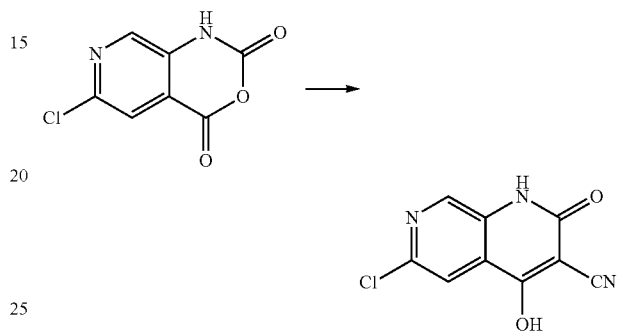

Triethylamine (35.182 g, 0.3478 mol, 2 eq) and ethyl cyanoacetate (19.665 g, 0.1738 mol) were added to the above-mentioned reaction liquid, and reacted at 150° C. for 3 h; LC-MS monitoring showed that the reaction was complete, and then the reaction liquid was cooled down to room temperature and concentrated under reduced pressure; water (200 mL) was added, and the mixture was adjusted to pH 1 with hydrochloric acid (1 mol/L), stirred for 15 minutes, and filtered by suction; and the filter cake was washed twice with EA, and dried at 40° C. to obtain a product as a light brick-red solid (25.655 g, yield: 66%).

Step 3: Synthesis of 4,6-dichloro-2-oxo-1,2-dihydro-1,7-diazanaphthalene-3-carbonitrile

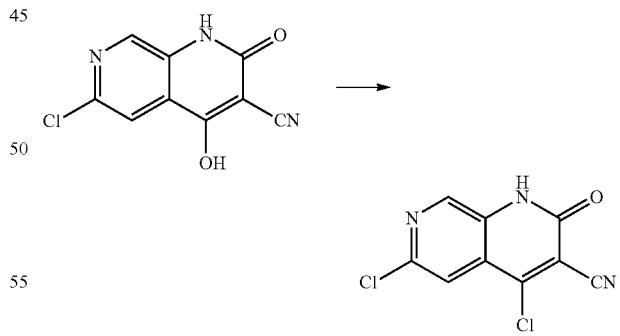

6-chloro-4-hydroxyl-2-oxo-1,2-dihydro-1,7-diazanaphthalene-3-carbonitrile (5.0 g, 0.0226 mol, 1 eq) and phosphorus oxychloride (15 mL) were added to a reaction flask; the reaction flask was put into an oil bath already heated to 100° C. for reaction for about 6 min; and the solid started to dissolve slowly, and the color gradually deepened from light yellow. TLC detection showed that the reaction was completed, and cooled to room temperature; an appropriate amount of DCM was added to the flask, and the mixture was poured into ice water (100 mL), stirred for 10 min, and filtered by suction; and the filter cake was washed with methyl tert-butyl ether, drained off, and dried in vacuum at 40° C. to obtain a product as a light yellow solid. The materials were fed in five batches, and a total of 25.655 g (0.1157 mol) of 6-chloro-4-hydroxyl-2-oxo-1,2-dihydro-1,7-diazanaphthalene-3-carbonitrile was fed to obtain 19.486 g of the product (yield: 70.1%).

Example 1 Preparation of a Compound of Formula (I)

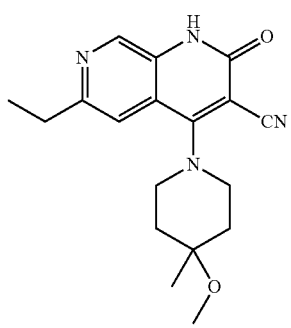 [SMILES: CCc1cc2c(N3CCC(C)(OC)CC3)c(C#N)c(=O)[nH]c2cn1]

Step 1: Synthesis of 6-chloro-4-(4-methoxy-4-methylpiperidin-1-yl)-2-oxo-1,2-dihydro-1,7-diazanaphthalene-3-carbonitrile

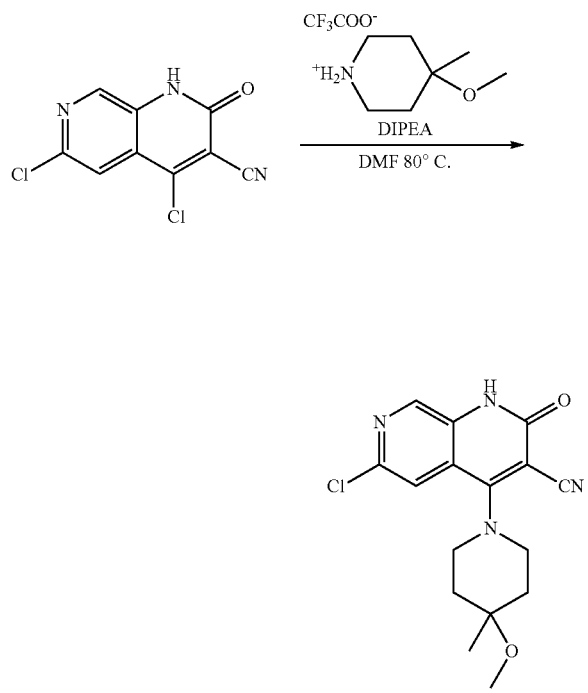

The intermediate 4,6-dichloro-2-oxo-1,2-dihydro-1,7-diazanaphthalene-3-carbonitrile (2.0 g, 8.33 mmol, 1.0 eq) was dissolved in DMF (10 mL); DIPEA (6.45 g, 50 mmol, 6.0 eq) and 4-methoxy-4-methylpiperidine trifluoroacetate (2.2 g, 9.16 mmol, 1.1 eq) were added; and the mixture was reacted at 80° C. for 2 hours. LC-MS detection showed that the reaction was complete; water (10 mL) was added, and the mixture was extracted with dichloromethane (10 mL×3); the organic phase was washed with water (10 mL×3), dried over anhydrous sodium sulfate, filtered, and concentrated under reduced pressure to obtain a product as a yellow solid (2.7 g crude).

$^1$H NMR (400 MHz, DMSO-$d_6$) δ(ppm): 12.11 (s, 1H), 8.45 (s, 1H), 7.61 (s, 1H), 3.61-3.59 (m, 4H), 3.18 (s, 3H), 1.91-1.88 (m, 2H), 1.81-1.76 (m, 2H), 1.21 (s, 3H).

Molecular formula: $C_{16}H_{17}N_4O_2Cl$ Molecular weight: 332.79 LC-MS (Pos, m/z)=333.7[M+H]$^+$ Step 2: Synthesis of 4-(4-methoxy-4-methylpiperidin-1-yl)-2-oxo-6-vinyl-1,2-dihydro-1,7-diazanaphthalene-3-carbonitrile

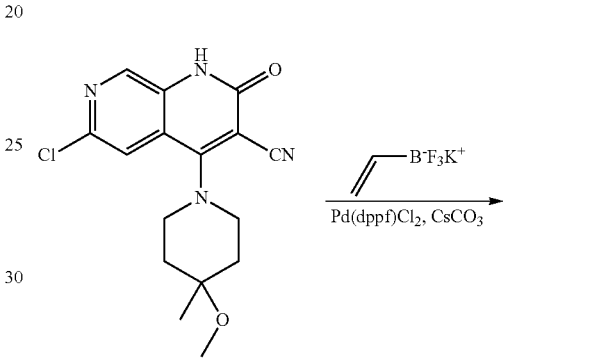

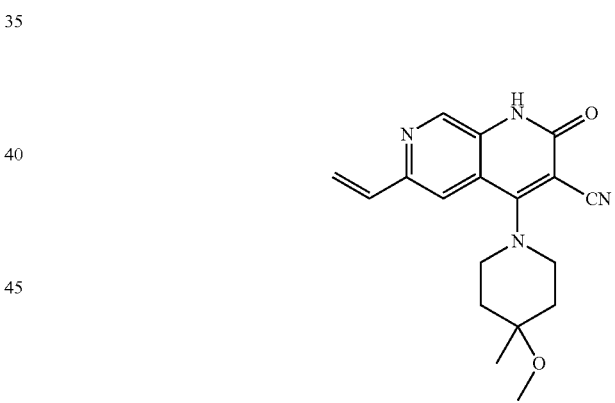

The intermediate 6-chloro-4-(4-methoxy-4-methylpiperidin-1-yl)-2-oxo-1,2-dihydro-1,7-diazanaphthalene-3-carbonitrile (2.7 g crude, 8.11 mmol, 1.0 eq) was dissolved in 1,4-dioxane (20 mL) and H$_2$O (5 mL); potassium vinyltrifluoroborate (1.63 g, 12.17 mmol, 1.5 eq), cesium carbonate (3.965 g, 12.17 mmol, 1.5 eq) and [1,1'-bis(diphenylphosphino)ferrocene]palladium dichloride (297 mg, 0.41 mmol, 0.05 eq) were added; and the mixture was reacted under nitrogen protection at 100° C. for 8 hours. LC-MS detection showed that the reaction was complete; water (20 mL) was added, and the mixture was extracted with dichloromethane (30 mL×3); the organic phase was dried over anhydrous sodium sulfate, filtered, and concentrated under reduced pressure; and the crude product was purified by silica gel column chromatography (DCM:MeOH=70:1) to obtain a product as a yellow solid (1.15 g, yield: 43%).

Step 3: Synthesis of 6-ethyl-4-(4-methoxy-4-methylpiperidin-1-yl)-2-oxo-1,2-dihydro-1,7-diazanaphthalene-3-carbonitrile

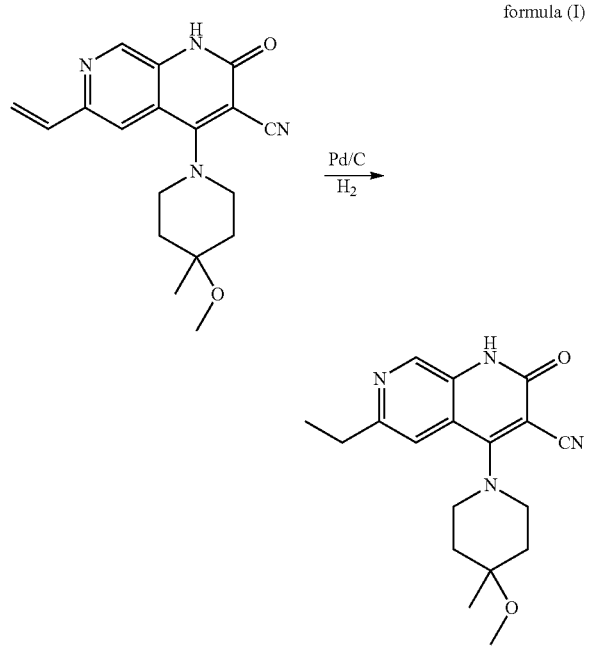

The intermediate 4-(4-methoxy-4-methylpiperidin-1-yl)-2-oxo-6-vinyl-1,2-dihydro-1,7-diazanaphthalene-3-carbonitrile (150 mg, 0.46 mmol, 1.0 eq) was dissolved in methanol (5 mL), and Pd/C (100 mg) was added; the mixture was subjected to hydrogen replacement three times, and reacted under a hydrogen atmosphere for 1 hour; and LC-MS detection showed that the reaction was complete. The mixture was filtered by suction, and the filtrate was concentrated under reduced pressure to obtain a product (120 mg, yield: 80%).

$^1$HNMR (400 MHz, DMSO-$d_6$) δ(ppm): 11.89 (s, 1H), 8.59 (s, 1H), 7.41 (s, 1H), 3.60-3.62 (m, 4H), 3.19 (s, 3H), 2.79-2.84 (m, 2H), 1.89-1.93 (m, 2H), 1.75-1.82 (m, 2H), 1.22-1.27 (m, 6H).

Molecular formula: $C_{18}H_{22}N_4O_2$ Molecular weight: 326.40 LC-MS (Pos, m/z)=327.26[M+H]$^+$.

Example 2 Preparation of a Crystal Form I of a Compound of Formula (I)

To a 50 L reaction kettle was added ethanol (21 L, 30 V), and 985 g of the compound of formula (I) was added to the reaction system; the reaction system was heated to reflux, and stirred for 1 hour until the system was completely dissolved; the system was added with activated carbon (70 g, 10%), stirred for half an hour, and filtered while hot to remove activated carbon and impurities; raising the temperature of the filtrate until the system was completely dissolved; ethanol was distilled off under reduced pressure; and the resultant was refluxed and stirred until the temperature was naturally cooled down to room temperature for crystallization.

The X-ray powder diffraction pattern of the crystal form I comprises characteristic peaks at 7.3±0.2, 13.6±0.2, 14.5±0.2°, 18.0±0.2°, 19.1±0.2, 22.0±0.2° and 23.4±0.2° 2θ (°), comprises characteristic peaks at 14.2±0.2, 16.1±0.2°, 19.4±0.2° and 25.6±0.2° 2θ (°), and further comprises characteristic peaks at 15.1±0.2° and 17.6±0.2° 2θ (°), as determined by using Cu-Kα radiation. XRPD analysis is as shown in FIG. 1.

Figure 2:
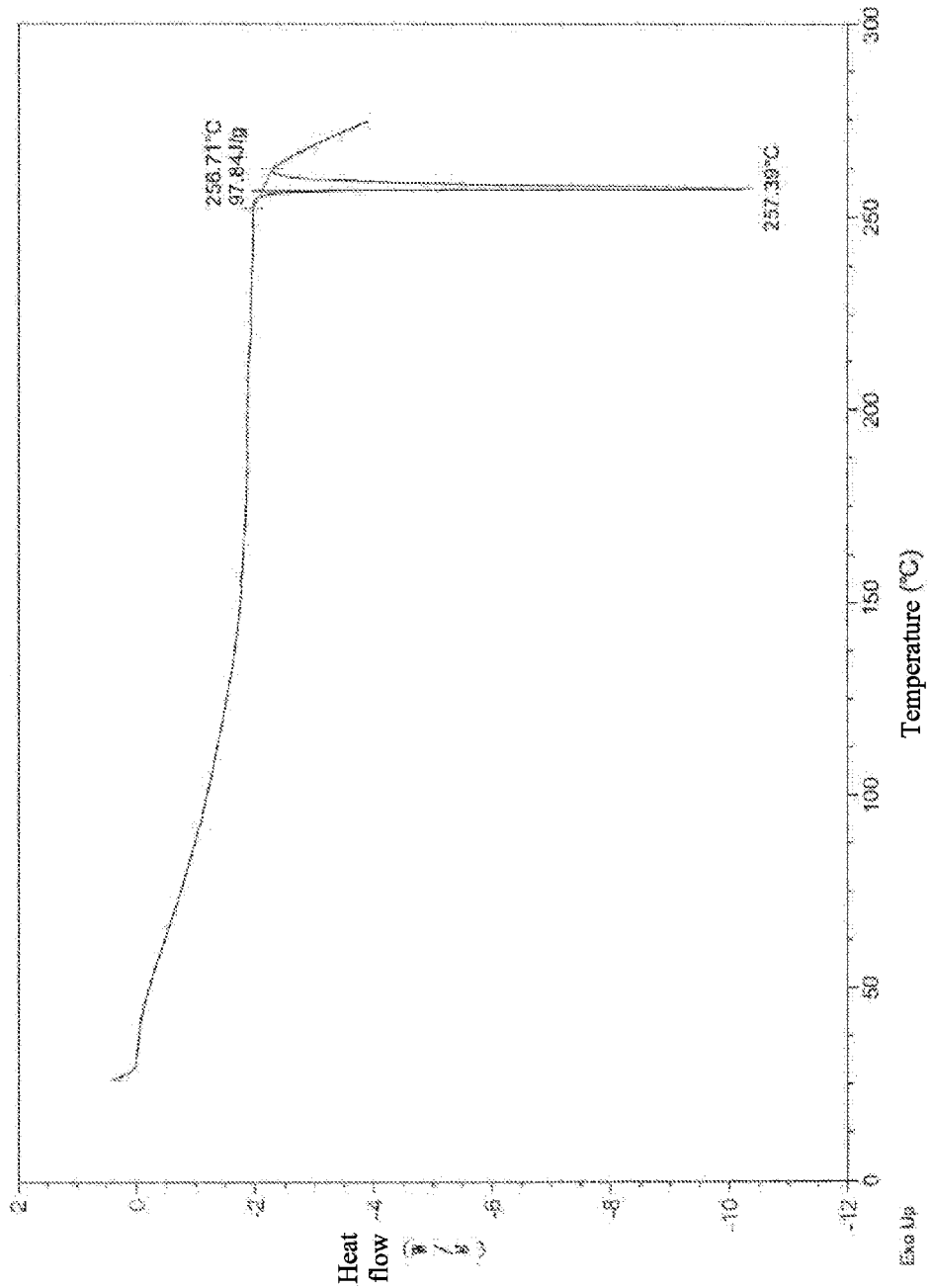
FIG. 2 is a differential scanning calorimetry (DSC) pattern of the crystal form I of the compound of formula (I).

The melting temperature as measured by a differential scanning calorimeter of the crystal form I is about 256° C.-258° C., which is as shown in FIG. 2.

Example 3 Preparation of a Crystal Form I of a Compound of Formula (I)

1 g of the compound of formula (I) was taken and dissolved in 20 mL of methanol; the mixture was heated to reflux until the system was completely dissolved; and the resultant was volatilized to dryness at 50° C. to obtain the crystal form I.

Figure 3:
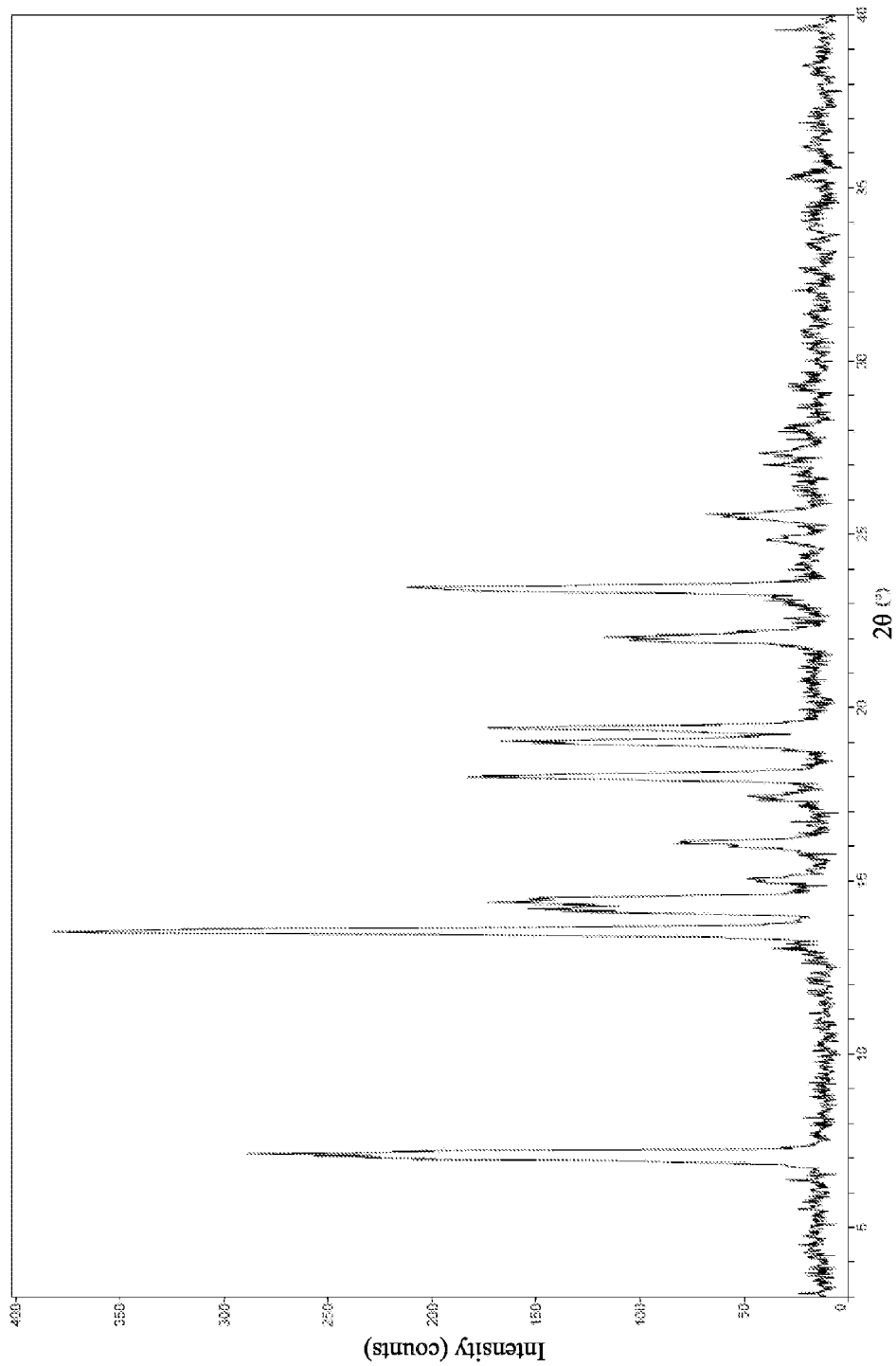
FIG. 3 is an X-ray powder diffraction (XRPD) pattern of the crystal form I of the compound of formula (I).

The X-ray powder diffraction pattern of the crystal form I comprises characteristic peaks at 7.3±0.2, 13.6±0.2, 14.5±0.2°, 18.0±0.2°, 19.1±0.2, 22.0±0.2° and 23.4±0.2° 2θ (°), comprises characteristic peaks at 14.2±0.2, 16.1±0.2°, 19.4±0.2° and 25.6±0.2° 2θ (°), and further comprises characteristic peaks at 15.1±0.2° and 17.6±0.2° 2θ (°), as determined by using Cu-Kα radiation. XRPD analysis is as shown in FIG. 3.

Example 4 Preparation of a Crystal Form I of a Compound of Formula (I)

1 g of the compound of formula (I) was taken and dissolved in 20 mL of dichloromethane, and then 30 mL of acetone was added; and the mixture was evaporated at 50° C. to remove 30 mL of solvent, added with additional 30 mL of acetone, and volatilized to dryness at 50° C. to obtain the crystal form I.

Example 5 Preparation of a Crystal Form I of a Compound of Formula (I)

1 g of the compound of formula (I) was taken and dissolved in 20 mL of dichloromethane, and then 30 mL of acetonitrile was added; and the mixture was evaporated at 50° C. to remove 30 mL of solvent, added with additional 30 mL of acetonitrile, and volatilized to dryness at 50° C. to obtain the crystal form I.

Example 6 Preparation of a Crystal Form I of a Compound of Formula (I)

1 g of the compound of formula (I) was taken and dissolved in 20 mL of dichloromethane, and then 20 mL of ethyl acetate was added; the mixture was naturally volatilized at 15° C.-20° C. for 5 days until a solid was precipitated; and the solid was filtered by suction to obtain the crystal form I.

Example 7 Preparation of a Crystal Form I of a Compound of Formula (I)

1 g of the compound of formula (I) was taken and dissolved in 20 mL of dichloromethane, and then 20 mL of methyl tert-butyl ether was added; the mixture was naturally volatilized at 15° C.-20° C. for 5 days until a solid was precipitated; and the solid was filtered by suction to obtain the crystal form I.

Example 8 Preparation of a Crystal Form I of a Compound of Formula (I)

1 g of the compound of formula (I) was taken and dissolved in 20 mL of dichloromethane, and then 20 mL of dichloromethane was added; and the mixture was naturally volatilized at 15° C.-20° C. for 5 days to directly obtain the crystal form I.

Figure 4:
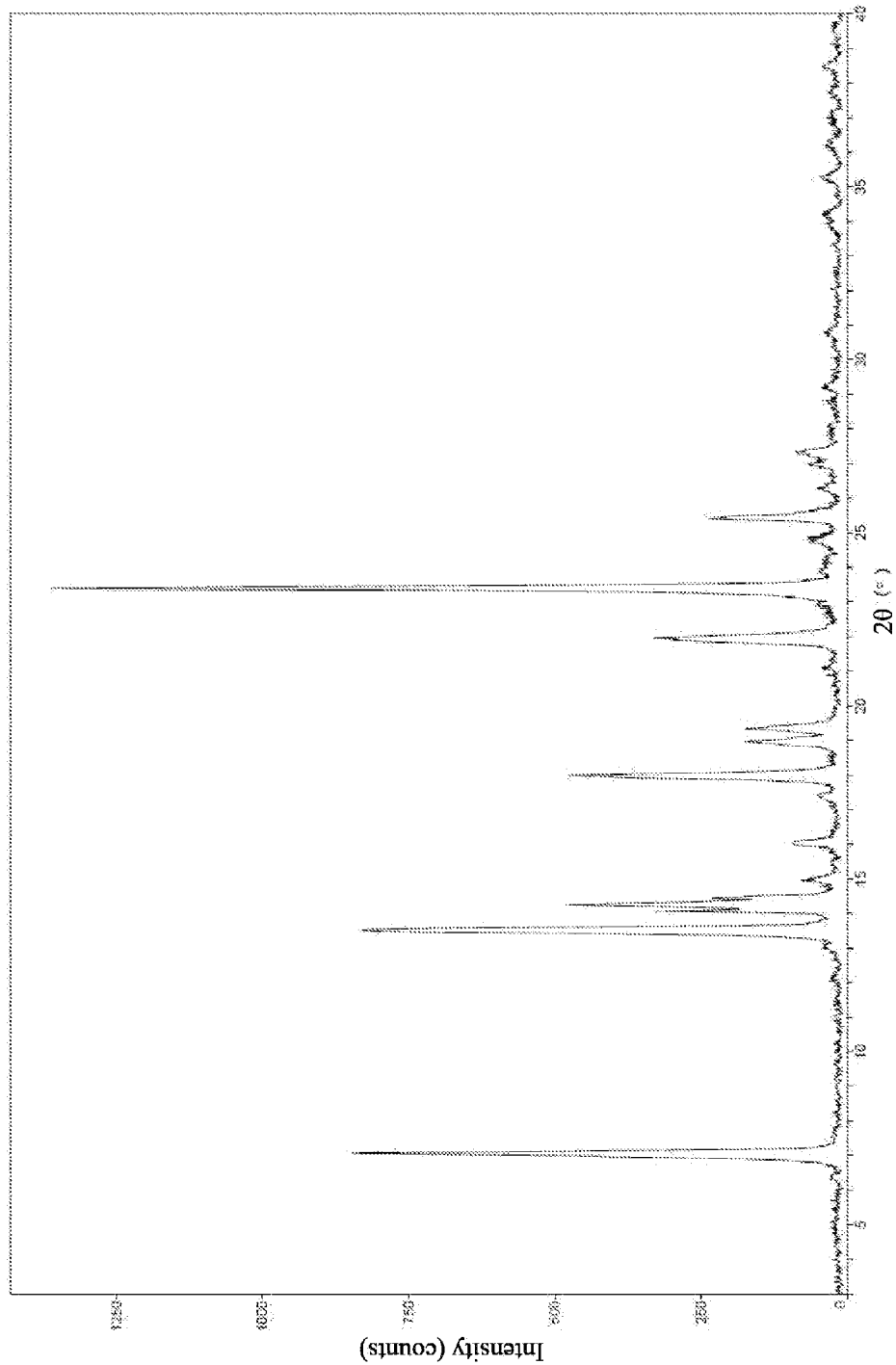
FIG. 4 is an X-ray powder diffraction (XRPD) pattern of the crystal form I of the compound of formula (I).

The X-ray powder diffraction pattern of the crystal form I comprises characteristic peaks at 7.3±0.2, 13.6±0.2, 14.5±0.2°, 18.0±0.2°, 19.1±0.2, 22.0±0.2° and 23.4±0.2° 2θ (°), comprises characteristic peaks at 14.2±0.2, 16.1±0.2°, 19.4±0.2° and 25.6±0.2° 2θ (°), and further comprises characteristic peaks at 15.1±0.2° and 17.6±0.2° 2θ (°), as determined by using Cu-Kα radiation. XRPD analysis is as shown in FIG. 4.

Example 9 Preparation of a Crystal Form I of a Compound of Formula (I)

1 g of the compound of formula (I) was taken and dissolved in 20 mL of dichloromethane, and then 20 mL of tetrahydrofuran was added; the mixture was naturally volatilized at 15° C.-20° C. for 5 days until a solid was precipitated; and the solid was filtered by suction to obtain the crystal form I.

Example 10 Preparation of a Crystal Form I of a Compound of Formula (I)

1 g of the compound of formula (I) was taken and dissolved in 20 mL of dichloromethane, and then 20 mL of ethanol was added; the mixture was naturally volatilized at 15° C.-20° C. for 5 days until a solid was precipitated; and the solid was filtered by suction to obtain the crystal form I.

Example 11 Preparation of a Crystal Form I of a Compound of Formula (I)

1 g of the compound of formula (I) was taken and dissolved in 20 mL of dichloromethane, and then 20 mL of isopropanol was added; the mixture was naturally volatilized at 15° C.-20° C. for 5 days until a solid was precipitated; and the solid was filtered by suction to obtain the crystal form I.

Example 12 Preparation of a Crystal Form I of a Compound of Formula (I)

1 g of the compound of formula (I) was taken and dissolved in 20 mL of dichloromethane, and then 20 mL of toluene was added; the mixture was naturally volatilized at 15° C.-20° C. for 5 days until a solid was precipitated; and the solid was filtered by suction to obtain the crystal form I.

Example 13 Preparation of a Crystal Form I of a Compound of Formula (I)

1 g of the compound of formula (I) was taken and dissolved in 20 mL of dichloromethane, and then 20 mL (water:ethanol=1:4) was added; the mixture was naturally volatilized at 15° C.-20° C. for 5 days until a solid was precipitated; and the solid was filtered by suction to obtain the crystal form I.

Example 14 Preparation of a Crystal Form I of a Compound of Formula (I)

1 g of the compound of formula (I) was taken and dissolved in 20 mL of dichloromethane, and then 20 mL (water:isopropanol=3:2) was added; the mixture was naturally volatilized at 15° C.-20° C. for 5 days until a solid was precipitated; and the solid was filtered by suction to obtain the crystal form I.

Figure 5:
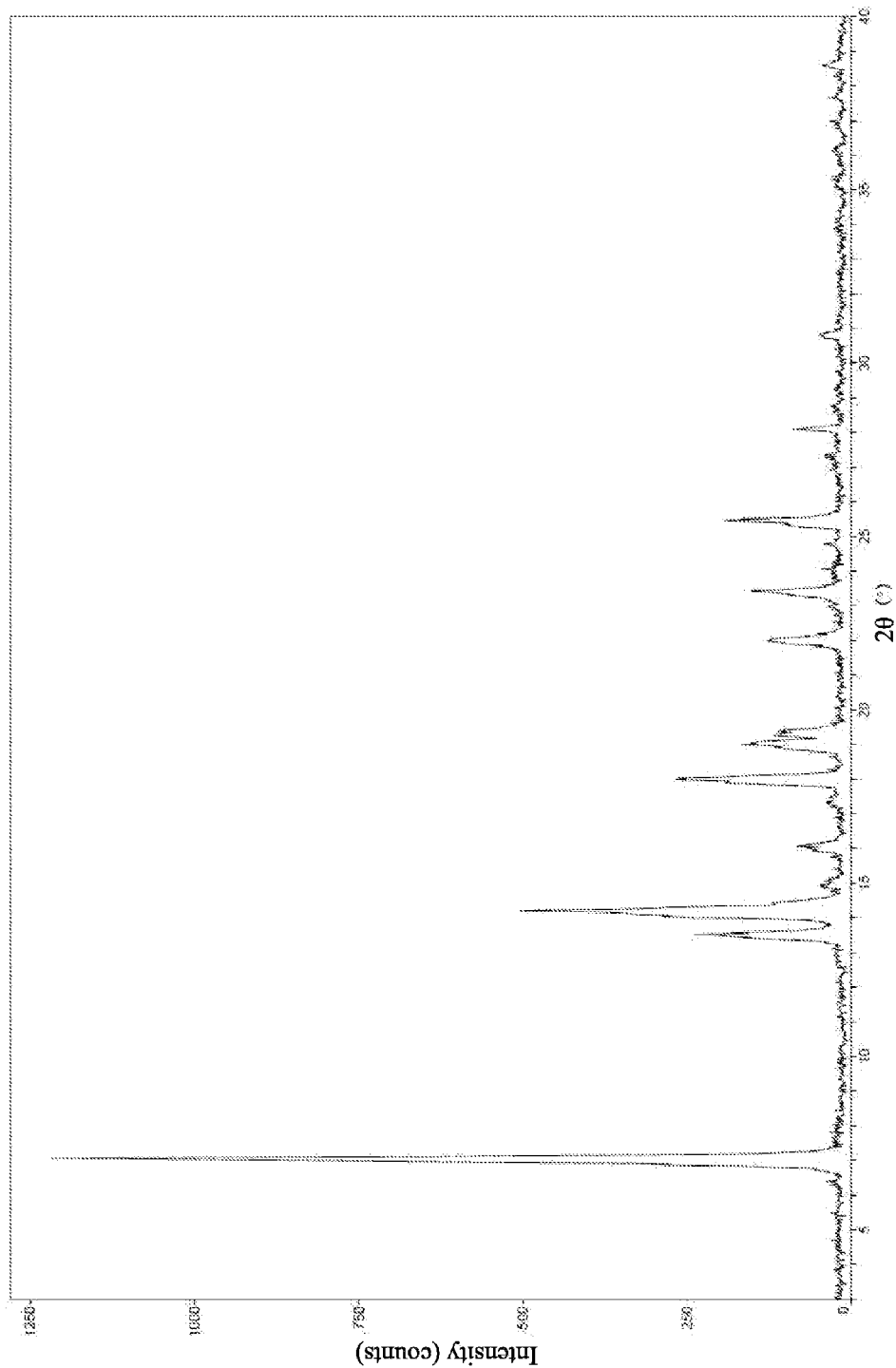
FIG. 5 is an X-ray powder diffraction (XRPD) pattern of the crystal form I of the compound of formula (I).

The X-ray powder diffraction pattern of the crystal form I comprises characteristic peaks at 7.3±0.2, 13.6±0.2, 14.5±0.2°, 18.0±0.2°, 19.1±0.2, 22.0±0.2° and 23.4±0.2° 2θ (°), comprises characteristic peaks at 14.2±0.2, 16.1±0.2°, 19.4±0.2° and 25.6±0.2° 2θ (°), and further comprises characteristic peaks at 15.1±0.2° and 17.6±0.2° 2θ (°), as determined by using Cu-Kα radiation. XRPD analysis is as shown in FIG. 5.

Example 15 Preparation of a Hydrochloride of a Compound of Formula (I)

At 45° C., 2 g of the compound of formula (I) was added to 1 mol/L hydrochloric acid solution (50 mL); the mixture was stirred for 15 min until the solid was completely dissolved to obtain a yellow clear solution; and after 2 min, a yellow solid was precipitated. The solution was slowly cooled down to room temperature until a large number of yellow solids were precipitated, and filtered by suction; and the filter cake was dried under reduced pressure at 40° C. to obtain 1.3 g of the hydrochloride of the compound of formula (I).

Example 16 Preparation of a Crystal Form II of a Compound of Formula (I)

Water was added to 200 mg of the hydrochloride of the compound of formula (I); the mixture was heated to 60° C. until complete dissolution, slowly cooled down under stirring for crystallization, and filtered by suction; and the filter cake was dried under reduced pressure at 40° C. to obtain the crystal form II.

Figure 6:
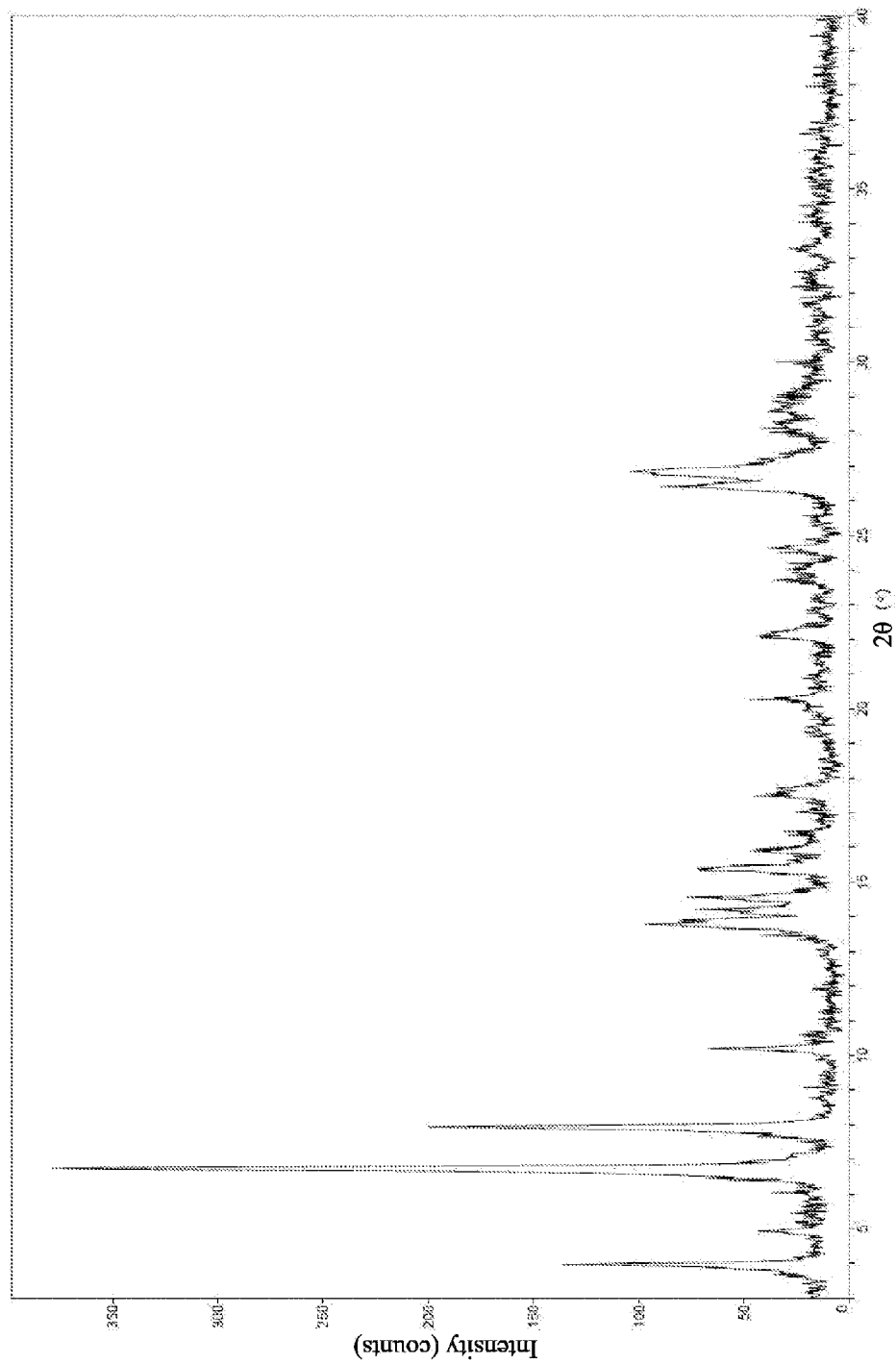
FIG. 6 is an X-ray powder diffraction (XRPD) pattern of the crystal form II of the compound of formula (I).

The X-ray powder diffraction pattern of the crystal form II comprises characteristic peaks at 4.0±0.2, 6.7±0.2, 7.9±0.2°, 13.5±0.2°, 14.2±0.2, 15.4±0.2°, 20.2±0.2° and 22.0±0.2° 2θ (°), and further comprises characteristic peaks at 10.2±0.2°, 13.8±0.2, 14.6±0.2, 26.40±0.2° and 26.80±0.2° 2θ (°), as determined by using Cu-Kα radiation. XRPD analysis is as shown in FIG. 6.

Example 17 Preparation of a Crystal Form II of a Compound of Formula (I)

To 200 mg of the hydrochloride of the compound of formula (I), 80% isopropanol (water:isopropanol=1:4) was added; the mixture was heated to 60° C. until complete dissolution, slowly cooled down under stirring for crystallization, and filtered by suction; and the filter cake was dried under reduced pressure at 40° C. to obtain the crystal form II.

Figure 7:
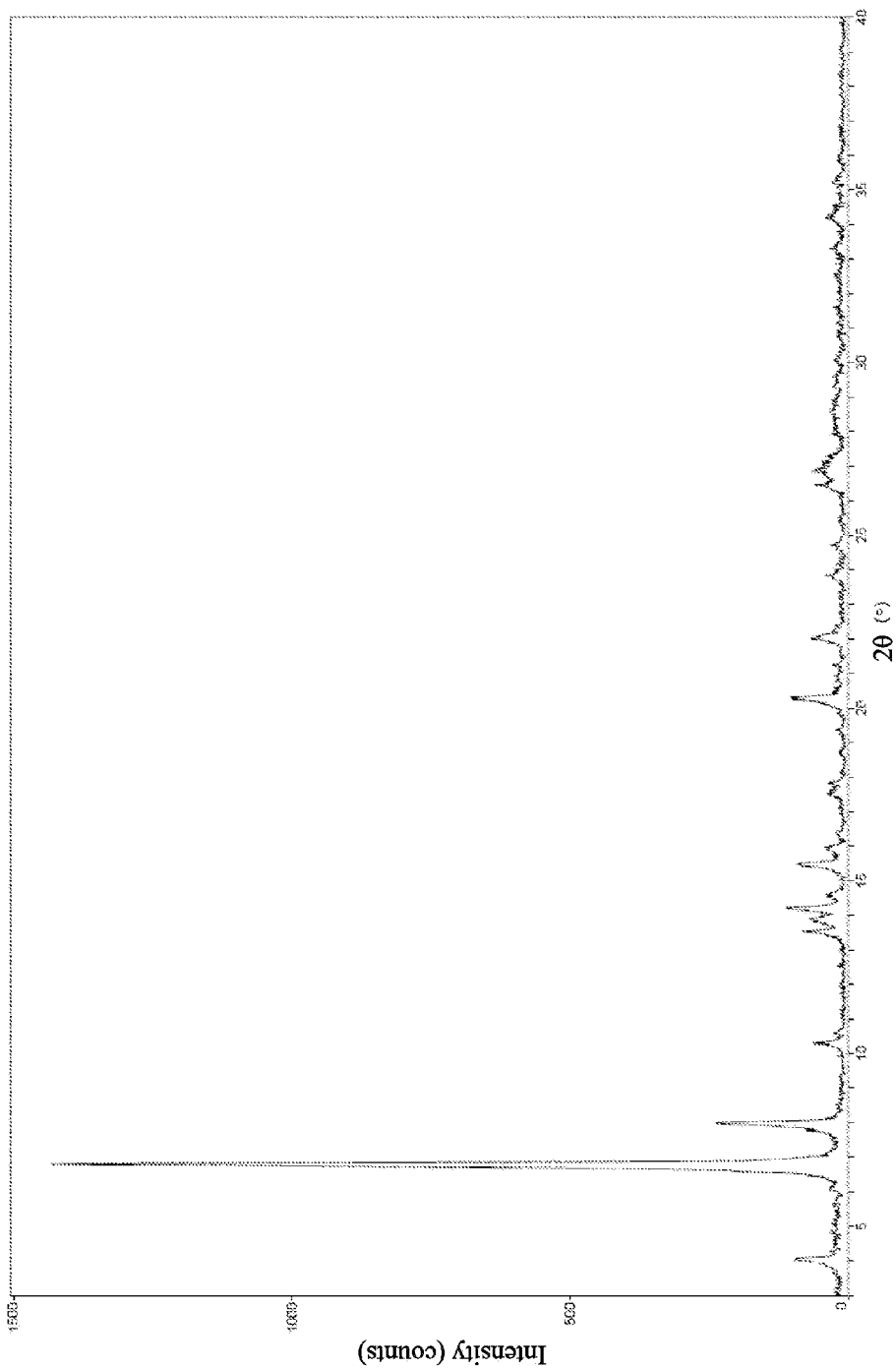
FIG. 7 is an X-ray powder diffraction (XRPD) pattern of the crystal form II of the compound of formula (I).

The X-ray powder diffraction pattern of the crystal form II comprises characteristic peaks at 4.0±0.2, 6.7±0.2, 7.9±0.2°, 13.5±0.2°, 14.2±0.2, 15.4±0.2°, 20.2±0.2° and 22.0±0.2° 2θ (°), and further comprises characteristic peaks at 10.2±0.2°, 13.8±0.2, 14.6±0.2, 26.40±0.2° and 26.80±0.2° 2θ (°), as determined by using Cu-Kα radiation. XRPD analysis is as shown in FIG. 7.

Example 18 Preparation of a Crystal Form II of a Compound of Formula (I)

Methanol was added to 200 mg of the hydrochloride of the compound of formula (I); the mixture was heated to 60°

C. until complete dissolution, slowly cooled down under stirring for crystallization, and filtered by suction; and the filter cake was dried under reduced pressure at 40° C. to obtain the crystal form II.

Figure 8:
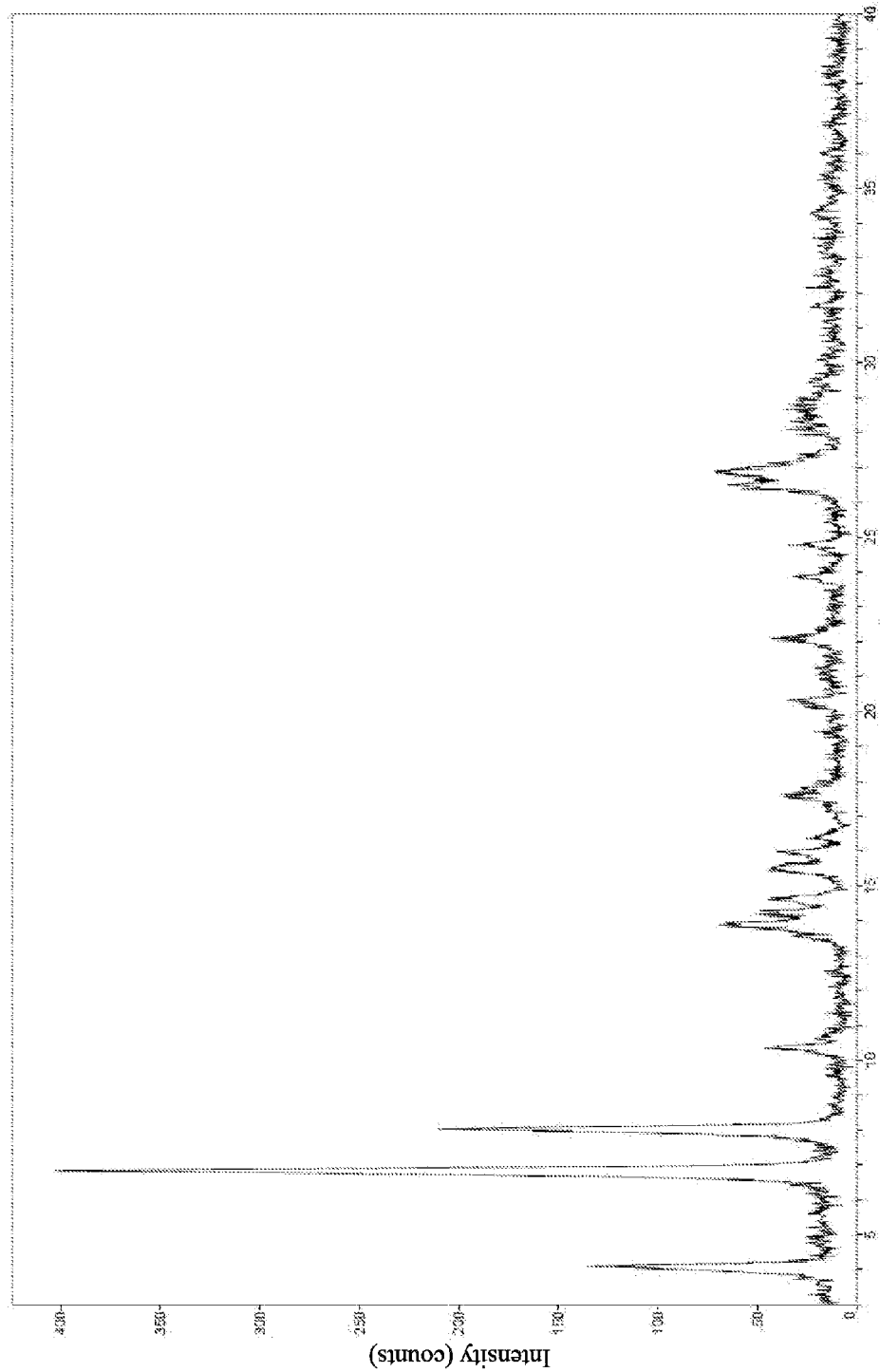
FIG. 8 is an X-ray powder diffraction (XRPD) pattern of the crystal form II of the compound of formula (I).

The X-ray powder diffraction pattern of the crystal form II comprises characteristic peaks at 4.0±0.2, 6.7±0.2, 7.9±0.2°, 13.5±0.2°, 14.2±0.2, 15.4±0.2°, 20.2±0.2° and 22.0±0.2° 2θ (°), and further comprises characteristic peaks at 10.2±0.2°, 13.8±0.2, 14.6±0.2, 26.40±0.2° and 26.80±0.2° 2θ (°), as determined by using Cu-Kα radiation. XRPD analysis is as shown in FIG. 8.

Example 19 Preparation of a Crystal Form II of a Compound of Formula (I)

Ethanol was added to 200 mg of the hydrochloride of the compound of formula (I); the mixture was heated to 60° C. until complete dissolution, slowly cooled down under stirring for crystallization, and filtered by suction; and the filter cake was dried under reduced pressure at 40° C. to obtain the crystal form II.

Example 20 Preparation of a Crystal Form III of a Compound of Formula (I)

Acetonitrile was added to 200 mg of the hydrochloride of the compound of formula (I); the mixture was heated to reflux until most of the solids were dissolved, and filtered by suction while hot; the filtrate was concentrated under reduced pressure until a large number of solids were precipitated, and filtered by suction; and the filter cake was dried under reduced pressure at 40° C. to obtain the crystal form III.

Figure 9:
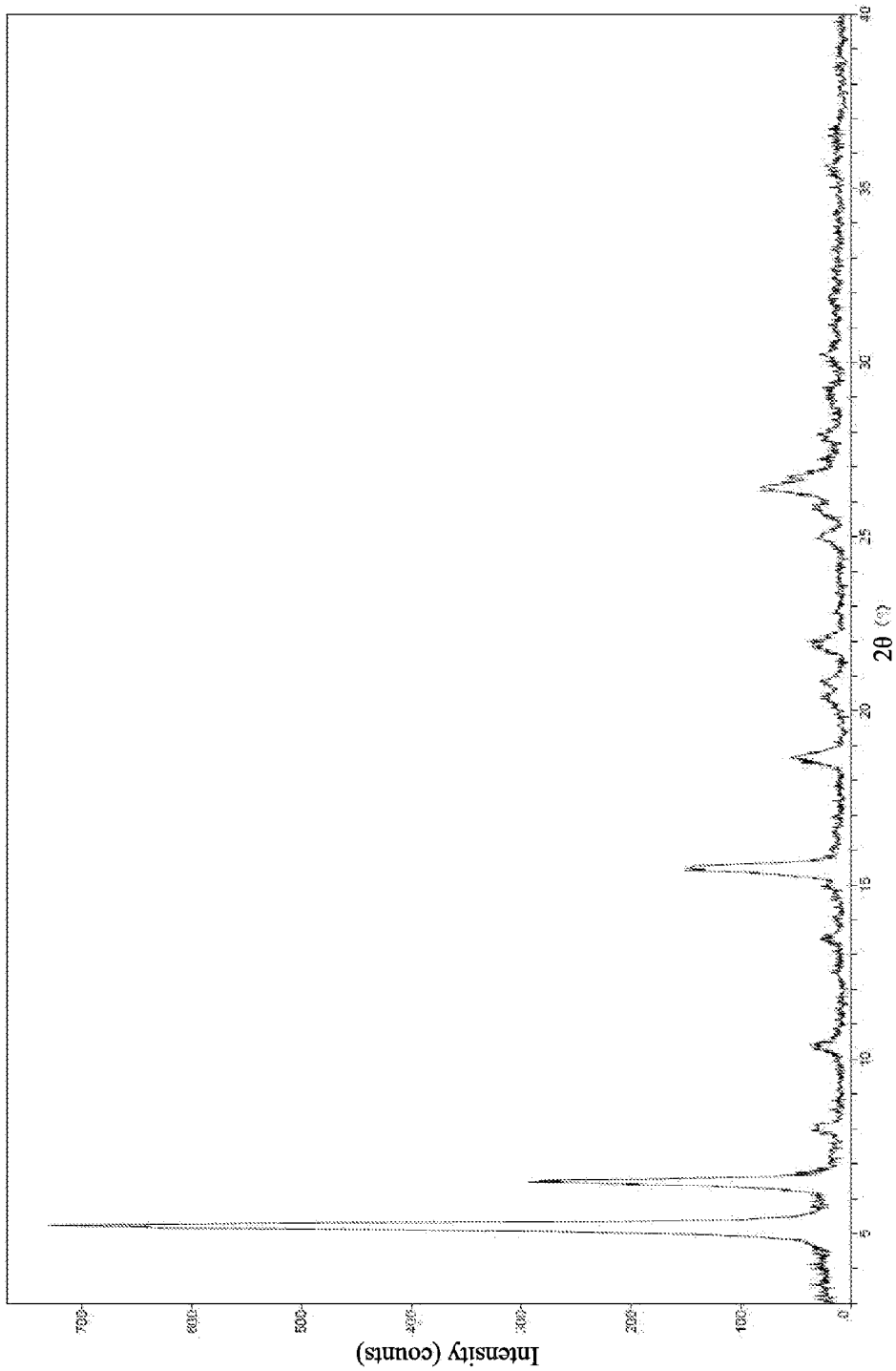
FIG. 9 is an X-ray powder diffraction (XRPD) pattern of the crystal form III of the compound of formula (I).

The X-ray powder diffraction pattern of the crystal form III comprises characteristic peaks at 5.2±0.2, 6.4±0.2, 15.3±0.2°, 18.6±0.2°, 22.0±0.2° and 26.4±0.2° 2θ (°), and further comprises characteristic peaks at 8.0±0.2°, 10.3±0.2, 13.5±0.2° and 25.0±0.2° 2θ (°), as determined by using Cu-Kα radiation. XRPD analysis is as shown in FIG. 9.

Example 21 Preparation of a Crystal Form III of a Compound of Formula (I)

Acetone was added to 200 mg of the hydrochloride of the compound of formula (I); the mixture was heated to 60° C. until most of the solids were dissolved, and filtered by suction while hot; the filtrate was concentrated under reduced pressure until a large number of solids were precipitated, and filtered by suction; and the filter cake was dried under reduced pressure at 40° C. to obtain the crystal form III.

Example 22 Preparation of a Crystal Form III of a Compound of Formula (I)

Ethyl acetate was added to 200 mg of the hydrochloride of the compound of formula (I); the mixture was heated to 60° C. until most of the solids were dissolved, and filtered by suction while hot; the filtrate was concentrated under reduced pressure until a large number of solids were precipitated, and filtered by suction; and the filter cake was dried under reduced pressure at 40° C. to obtain the crystal form III.

Figure 10:
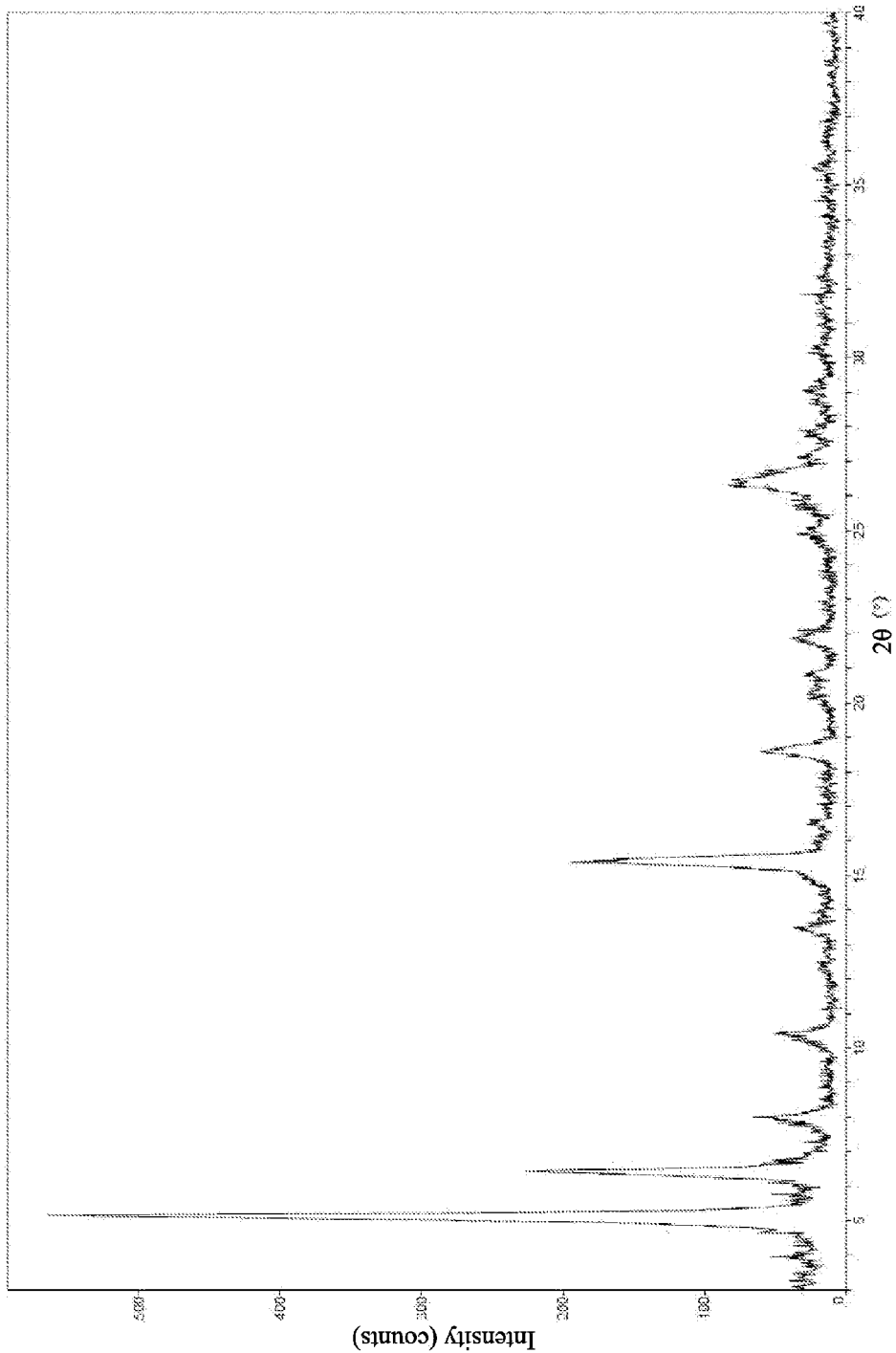
FIG. 10 is an X-ray powder diffraction (XRPD) pattern of the crystal form III of the compound of formula (I).

The X-ray powder diffraction pattern of the crystal form III comprises characteristic peaks at 5.2±0.2, 6.4±0.2, 15.3±0.2°, 18.6±0.2°, 22.0±0.2° and 26.4±0.2° 2θ (°), and further comprises characteristic peaks at 8.0±0.2°, 10.3±0.2°, 13.5±0.2° and 25.0±0.2° 2θ (°), as determined by using Cu-Kα radiation. XRPD analysis is as shown in FIG. 10.

Example 23 Preparation of a Crystal Form III of a Compound of Formula (I)

Tetrahydrofuran was added to 200 mg of the hydrochloride of the compound of formula (I); the mixture was heated to 60° C. until most of the solids were dissolved, and filtered by suction while hot; the filtrate was concentrated under reduced pressure until a large number of solids were precipitated, and filtered by suction; and the filter cake was dried under reduced pressure at 40° C. to obtain the crystal form III.

Figure 11:
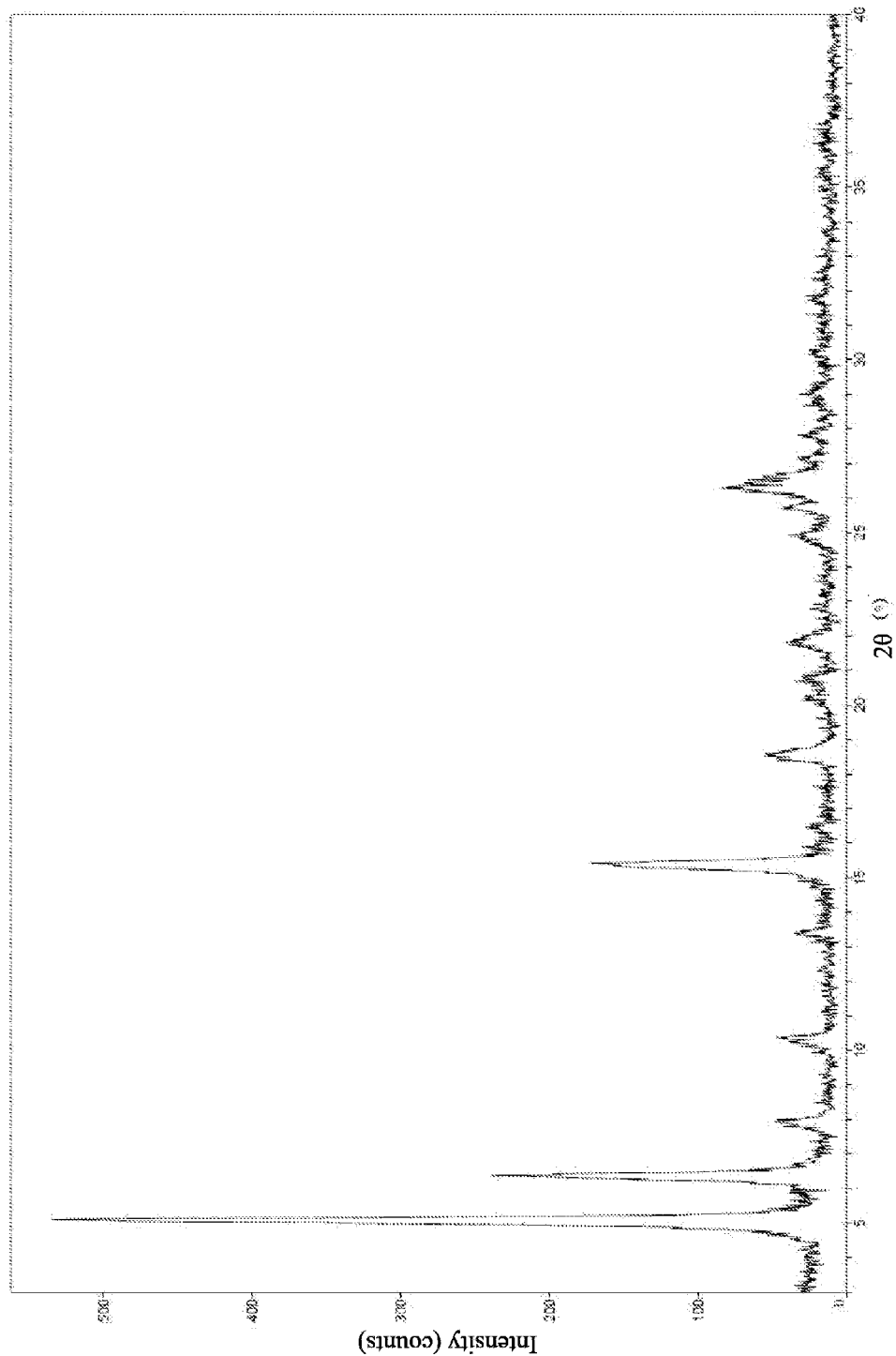
FIG. 11 is an X-ray powder diffraction (XRPD) pattern of the crystal form III of the compound of formula (I).

The X-ray powder diffraction pattern of the crystal form III comprises characteristic peaks at 5.2±0.2, 6.4±0.2, 15.3±0.2°, 18.6±0.2°, 22.0±0.2° and 26.4±0.2° 2θ (°), and further comprises characteristic peaks at 8.0±0.2°, 10.3±0.2, 13.5±0.2° and 25.0±0.2° 2θ (°), as determined by using Cu-Kα radiation. XRPD analysis is as shown in FIG. 11.

Example 24 Preparation of a Crystal Form IV of a Compound of Formula (I)

To 10 mL of 1 mol/L aqueous solution of p-toluenesulfonic acid, 1.3 g of the compound of formula (I) was added; and the mixture was heated to 50° C. until complete dissolution, and slowly cooled down to room temperature under stirring until a yellow solid was precipitated. The precipitates were filtered by suction, and the filter cake was washed with a small amount of water, filtered by suction for 1 hour, and dried under reduced pressure at 40° C. to obtain the crystal form IV.

Figure 12:
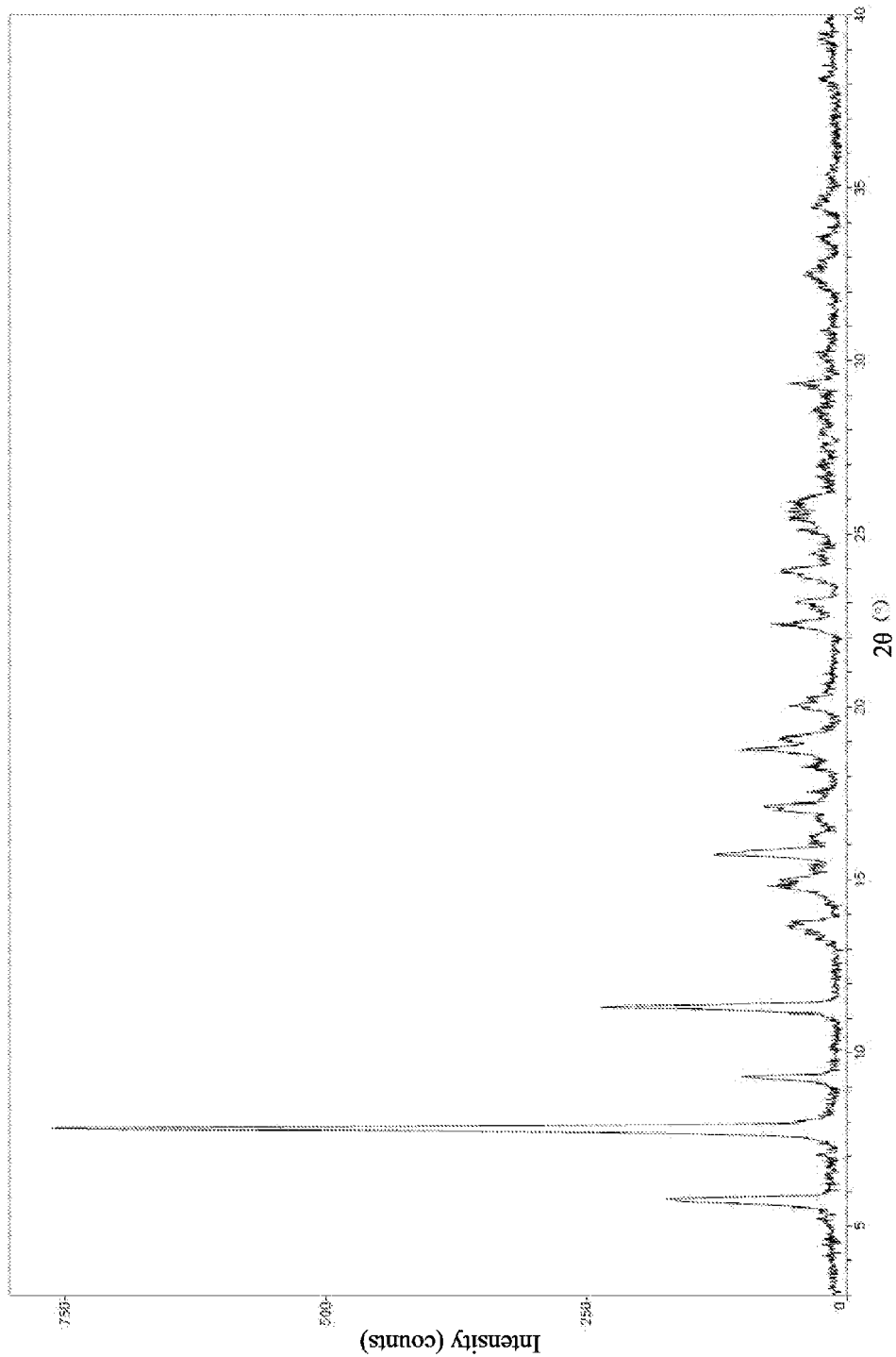
FIG. 12 is an X-ray powder diffraction (XRPD) pattern of the crystal form IV of the compound of formula (I).

The X-ray powder diffraction pattern of the crystal form IV comprises characteristic peaks at 5.8±0.2, 7.8±0.2, 9.3±0.2°, 11.3±0.2°, 13.7±0.2, 14.8±0.2° and 15.7±0.2° 2θ (°), and further comprises characteristic peaks at 17.1±0.2°, 18.7±0.2°, 20.0±0.2° and 22.4±0.2° 2θ (°), as determined by using Cu-Kα radiation. XRPD analysis is as shown in FIG. 12.

Example 25 Preparation of a Crystal Form V of a Compound of Formula (I)

To 10 mL of 1 mol/L aqueous solution of methanesulfonic acid, 1.3 g of the compound of formula (I) was added; the mixture was heated to 50° C. until complete dissolution, slowly cooled down to room temperature under stirring, added with methanol, and filtered by suction; and the filter cake was washed with a small amount of methanol, filtered by suction for 1 hour, and dried under reduced pressure at 40° C. to obtain the crystal form V.

Figure 13:
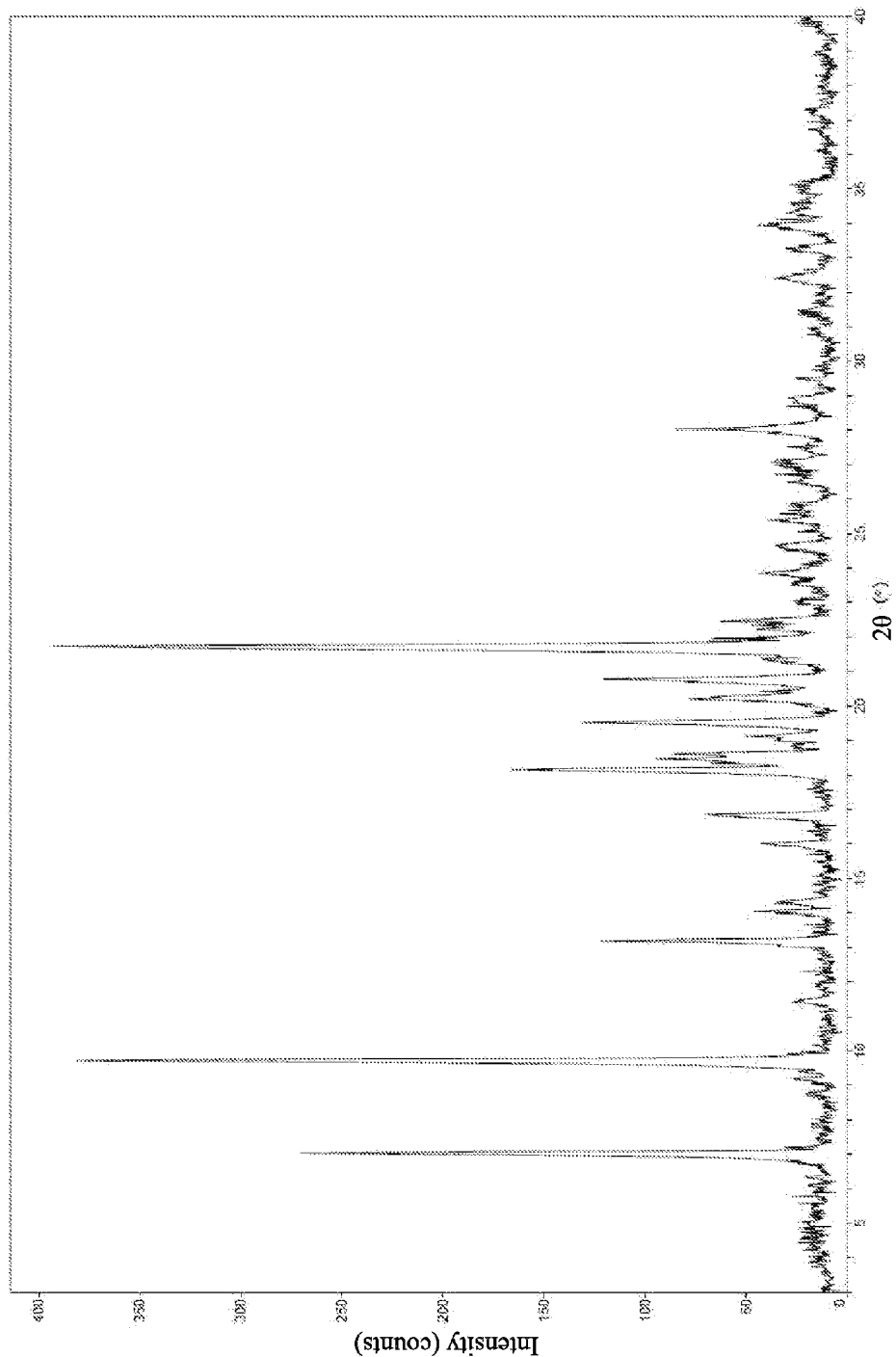
FIG. 13 is an X-ray powder diffraction (XRPD) pattern of the crystal form V of the compound of formula (I).

The X-ray powder diffraction pattern of the crystal form V comprises characteristic peaks at 7.0±0.2, 9.7±0.2, 13.2±0.2°, 18.1±0.2°, 19.5±0.2, 20.7±0.2° and 21.7±0.2° 2θ (°), and further comprises characteristic peaks at 16.9±0.2, 18.6±0.2°, 19.1±0.2°, 20.2±0.2° and 28.0±0.2° 2θ (°), as determined by using Cu-Kα radiation. XRPD analysis is as shown in FIG. 13.

Experimental Example 26 Preparation of a Crystal Form VI of a Compound of Formula (I)

The raw material 6-ethyl-4-(4-methoxy-4-methylpiperidin-1-yl)-2-oxo-1,2-dihydro-1,7-diazanaphthal ene-3-carbonitrile (10 g, 30.63 mmol, 1.0 eq) was added batchwise to sulfuric acid (1 N) (40 mL) for dissolution, and the mixture was reacted for 1 hour; after the raw material was dissolved to yield a clear solution, heating was stopped; the solution was cooled down to room temperature until a large number of solids were precipitated, and filtered by suction; and the filter cake was dried at 50° C. to obtain 6.9 g of the sulfate of the compound of formula (I), i.e., crystal form VI.

Figure 14:
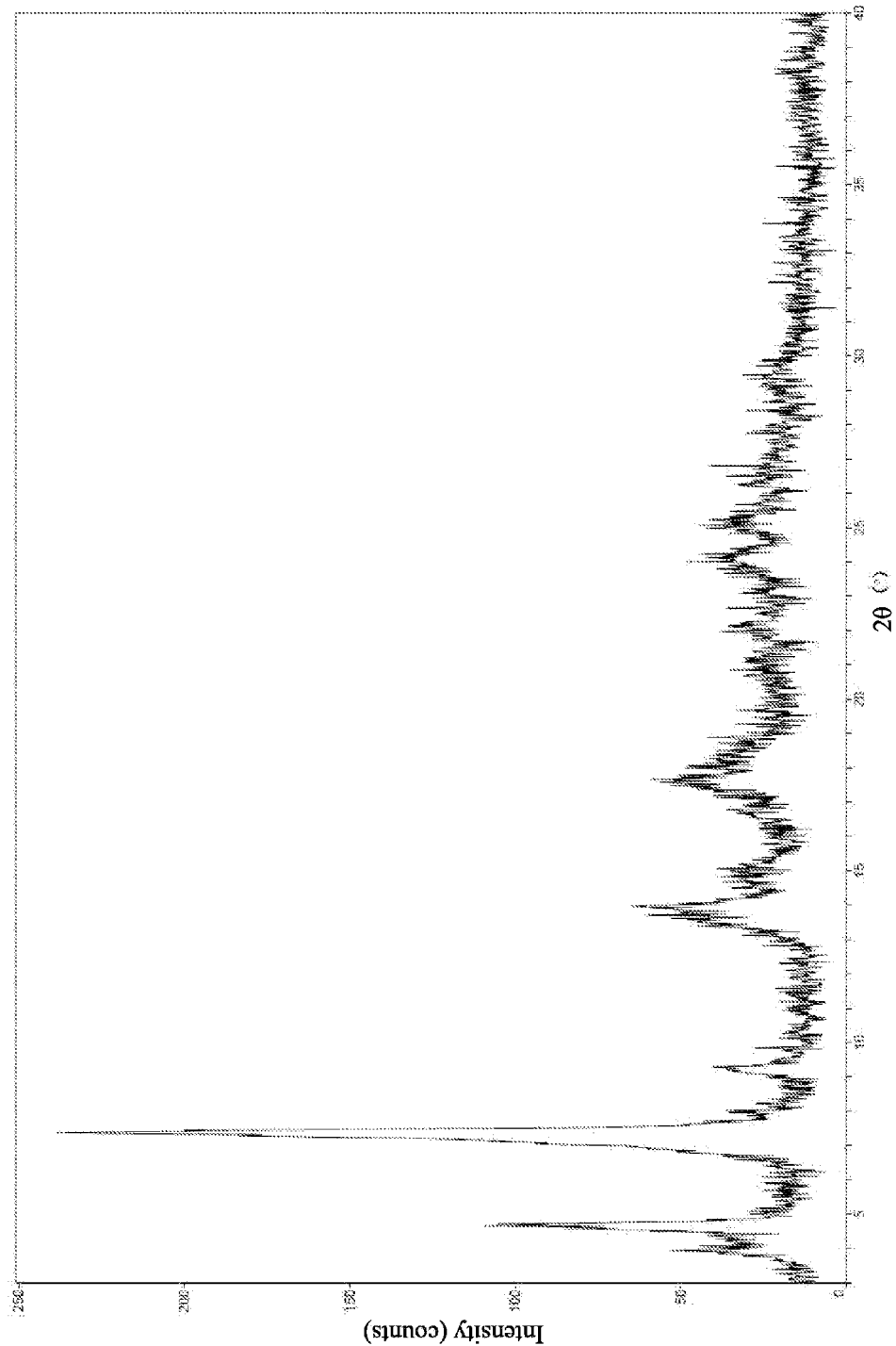
FIG. 14 is an X-ray powder diffraction (XRPD) pattern of the crystal form VI of the compound of formula (I).

The X-ray powder diffraction pattern of the crystal form VI comprises characteristic peaks at 4.4±0.2, 7.1±0.2, 8.8±0.2°, 14.3±0.2°, 17.8±0.2, 19.6±0.2° and 21.6±0.2° 2θ (°), and further comprises characteristic peaks at 25.5±0.2° and 27.7±0.2 2θ (°), as determined by using Cu-Kα radiation. XRPD analysis is as shown in FIG. 14.

Example 27 Preparation of a Crystal Form VI of a Compound of Formula (I)

The sulfate of the compound of formula (I) (1 g, 2.36 mmol, 1.0 eq) was dissolved in acetone (50 mL) for reflux; the mixture was stirred for 3 h, and a clear solution was not achieved by dissolving; heating was stopped; the solution was cooled down to room temperature and filtered by suction; and the filter cake was dried at 50° C. to obtain the crystal form VI.

Figure 15:
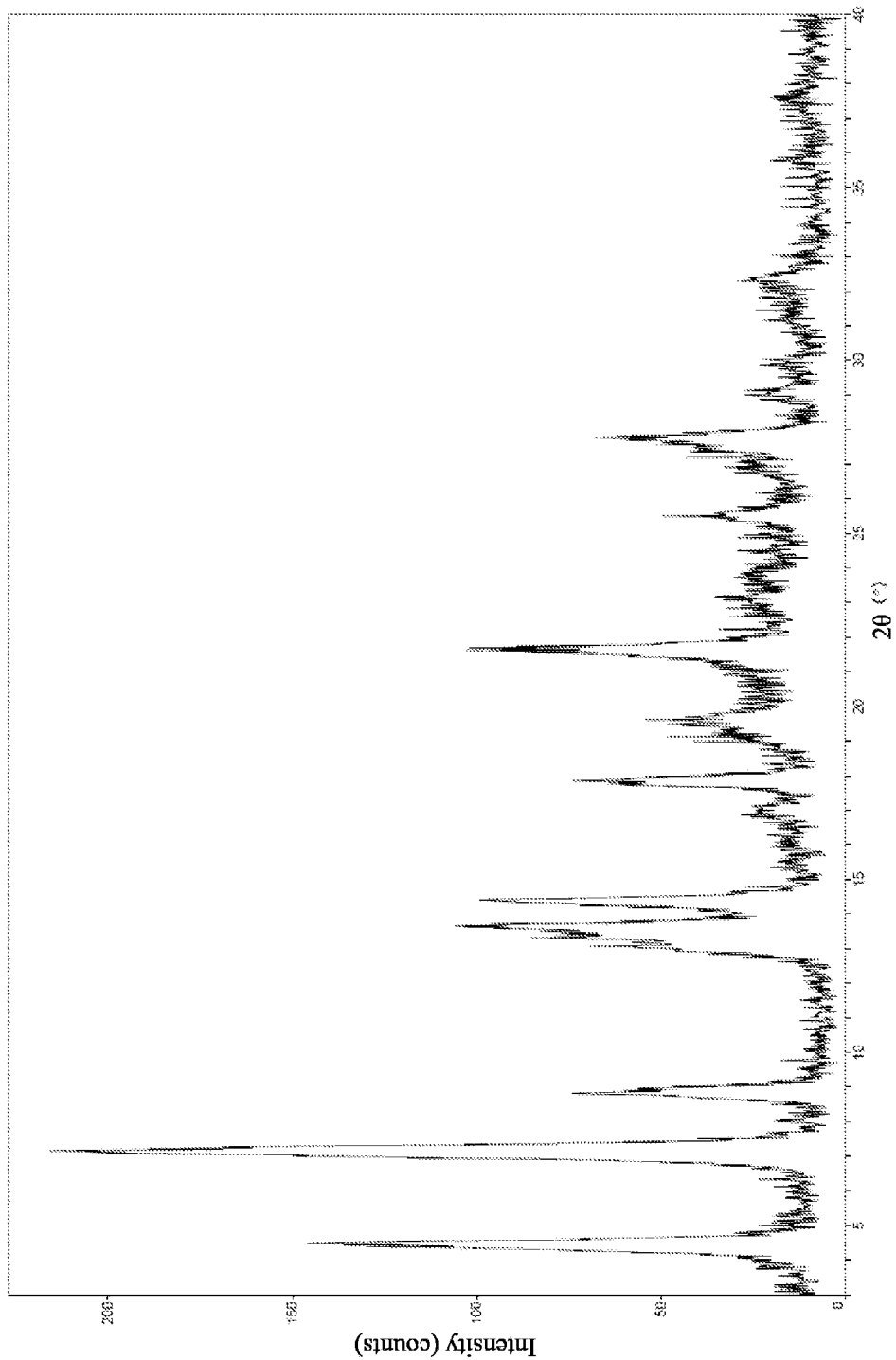
FIG. 15 is an X-ray powder diffraction (XRPD) pattern of the crystal form VI of the compound of formula (I).

The X-ray powder diffraction pattern of the crystal form VI comprises characteristic peaks at 4.4±0.2, 7.1±0.2, 8.8±0.2°, 14.3±0.2°, 17.8±0.2, 19.6±0.2° and 21.6±0.2° 2θ (°), and further comprises characteristic peaks at 25.5±0.2° and 27.7±0.2 2θ (°), as determined by using Cu-Kα radiation. XRPD analysis is as shown in FIG. 15.

Example 28 Preparation of a Crystal Form VI of a Compound of Formula (I)

The sulfate of the compound of formula (I) (1 g, 2.36 mmol, 1.0 eq) was dissolved in ethanol (15 mL) for reflux, and the mixture was stirred for 3 h; after the sulfate was dissolved to yield a clear solution, heating was stopped; the solution was cooled down to room temperature until a large number of solids were precipitated, and filtered by suction; and the filter cake was dried at 50° C. to obtain the crystal form VI.

Figure 16:
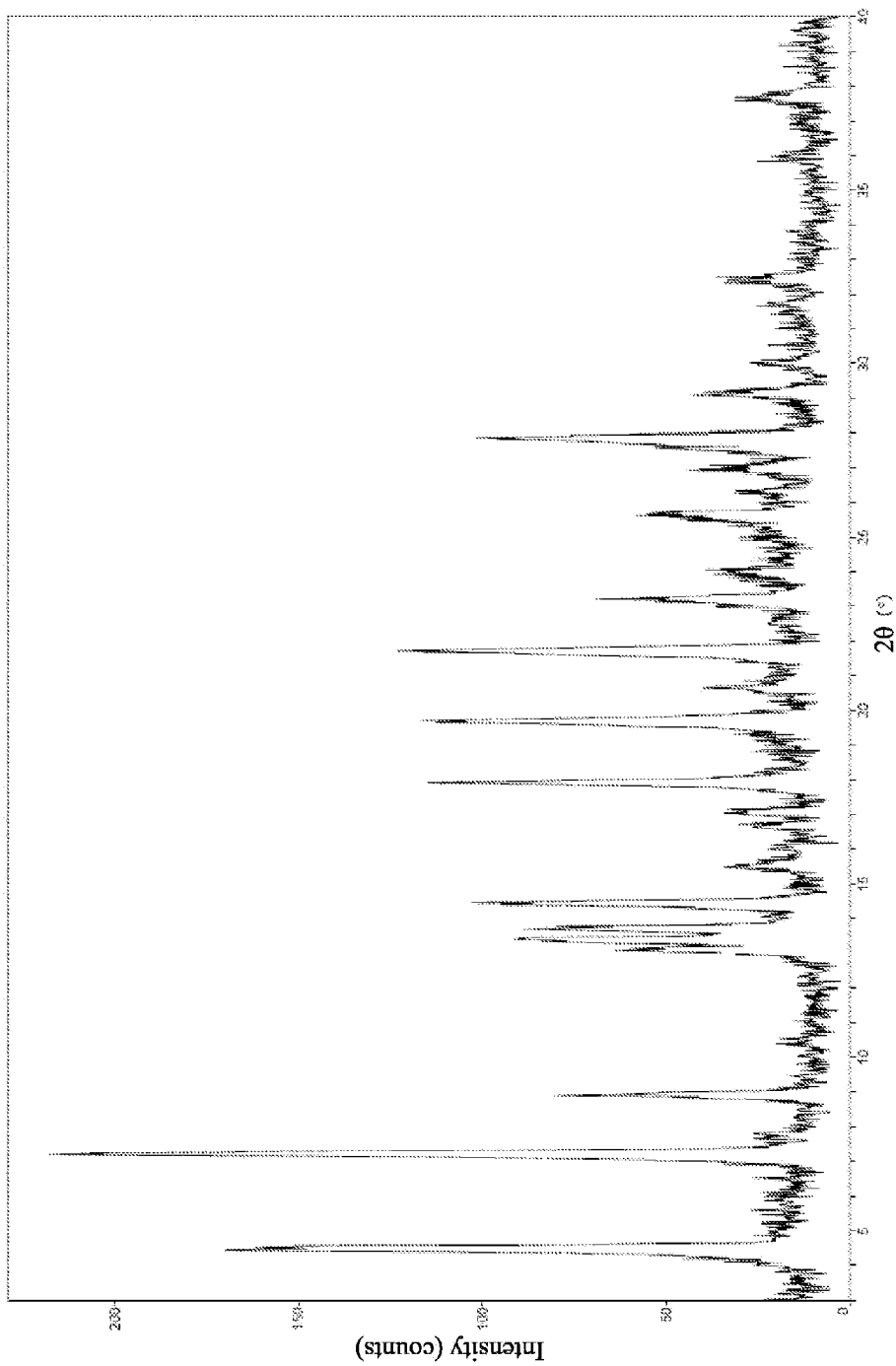
FIG. 16 is an X-ray powder diffraction (XRPD) pattern of the crystal form VI of the compound of formula (I).

The X-ray powder diffraction pattern of the crystal form VI comprises characteristic peaks at 4.4±0.2, 7.1±0.2, 8.8±0.2°, 14.3±0.2°, 17.8±0.2, 19.6±0.2° and 21.6±0.2° 2θ (°), and further comprises characteristic peaks at 25.5±0.2° and 27.7±0.2 2θ (°), as determined by using Cu-Kα radiation. XRPD analysis is as shown in FIG. 16.

Example 29 Preparation of a Crystal Form VI of a Compound of Formula (I)

The sulfate of the compound of formula (I) (1 g, 2.36 mmol, 1.0 eq) was dissolved in methanol (10 mL) for reflux, and the mixture was stirred for 3 h; after the sulfate was dissolved to yield a clear solution, heating was stopped; the solution was cooled down to room temperature until a large number of solids were precipitated, and filtered by suction; and the filter cake was dried at 50° C. to obtain the crystal form VI.

Example 30 Preparation of a Crystal Form VI of a Compound of Formula (I)

The sulfate of the compound of formula (I) (1 g, 2.36 mmol, 1.0 eq) was dissolved in tetrahydrofuran (50 mL) for reflux, and the mixture was stirred for 3 h; in the case that a dissolved clarification of the reaction was not achieved, heating was stopped; the solution was cooled down to room temperature and filtered by suction; and the filter cake was dried at 50° C. to obtain the crystal form VI.

Figure 17:
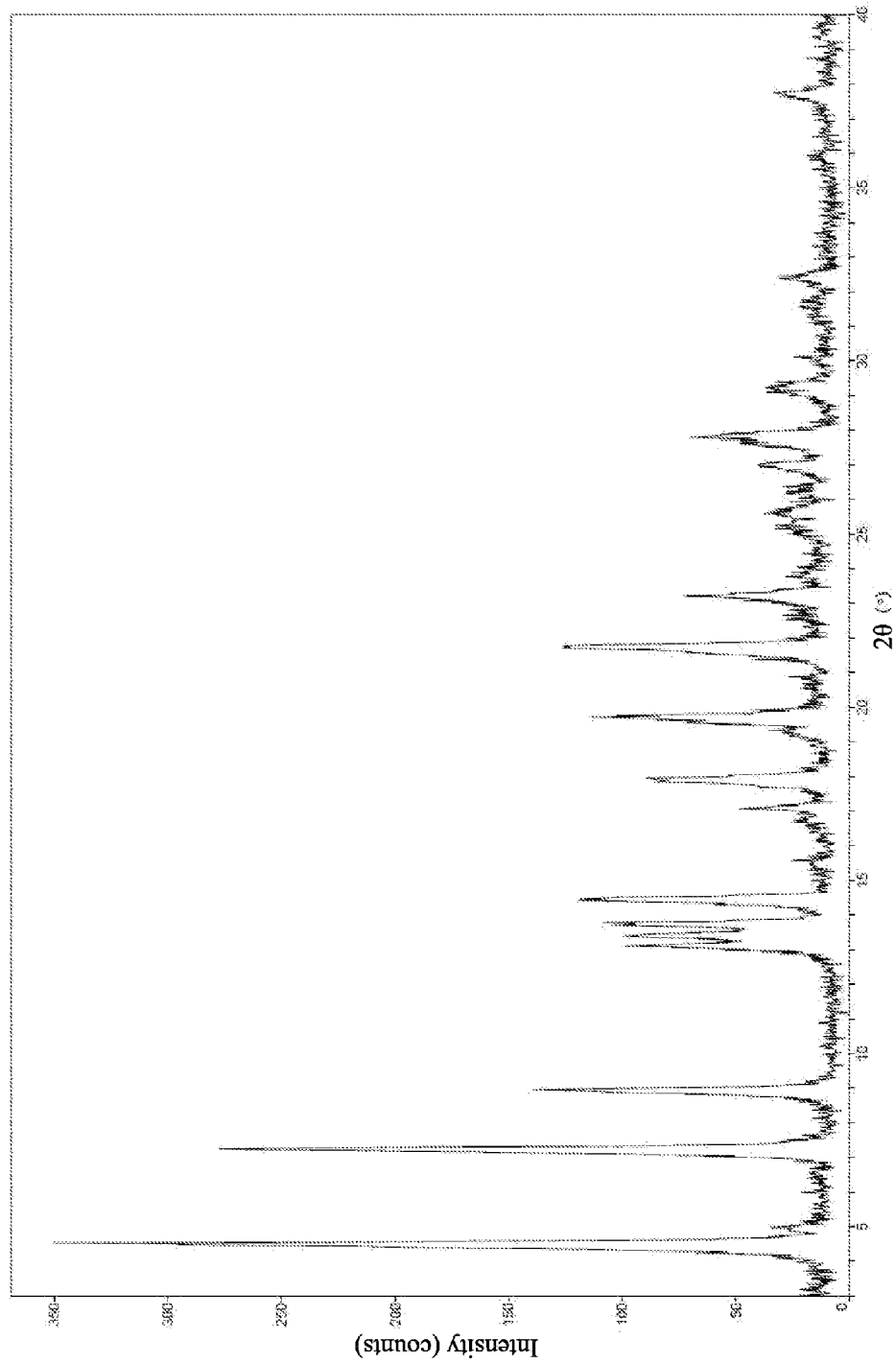
FIG. 17 is an X-ray powder diffraction (XRPD) pattern of the crystal form VI of the compound of formula (I).

The X-ray powder diffraction pattern of the crystal form VI comprises characteristic peaks at 4.4±0.2, 7.1±0.2, 8.8±0.2°, 14.3±0.2°, 17.8±0.2, 19.6±0.2° and 21.6±0.2° 2θ (°), and further comprises characteristic peaks at 25.5±0.2° and 27.7±0.2 2θ (°), as determined by using Cu-Kα radiation. XRPD analysis is as shown in FIG. 17.

Example 31 Preparation of a Crystal Form VII of a Compound of Formula (I)

The sulfate of the compound of formula (I) (1 g, 2.36 mmol, 1.0 eq) was dissolved in isopropanol (50 mL) for reflux, and the mixture was stirred for 3 h; after the sulfate was dissolved to yield a clear solution, heating was stopped; the solution was cooled down to room temperature until a large number of solids were precipitated, and filtered by suction; and the filter cake was dried at 50° C. to obtain the crystal form VII.

Figure 18:
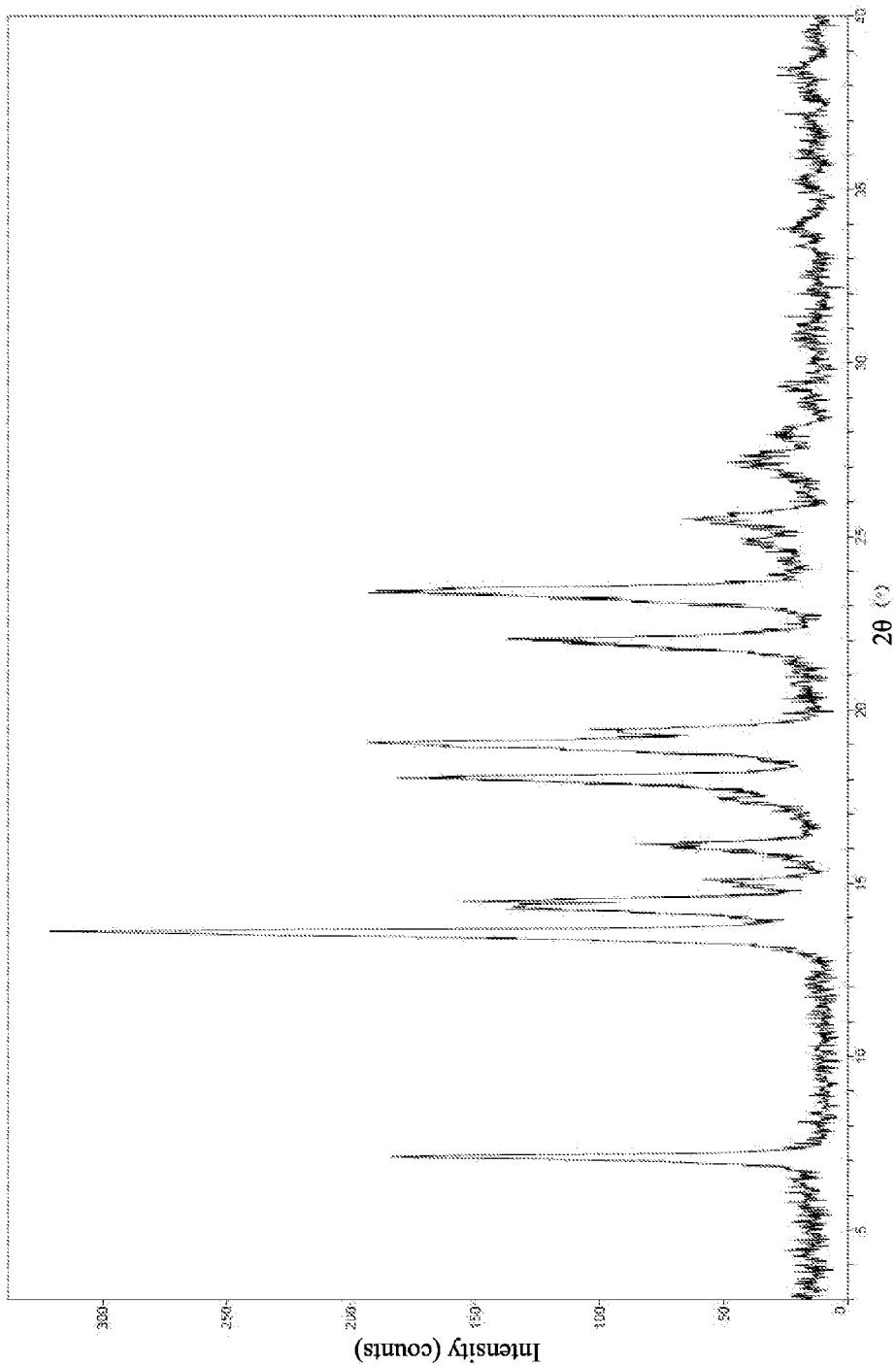
FIG. 18 is an X-ray powder diffraction (XRPD) pattern of the crystal form VII of the compound of formula (I).

The X-ray powder diffraction pattern of the crystal form VII comprises characteristic peaks at 7.1±0.2, 13.6±0.2, 14.5±0.2°, 18.0±0.2°, 19.0±0.2, 22.0±0.2° and 23.4±0.2° 2θ (°), and further comprises characteristic peaks at 15.0±0.2, 16.1±0.2°, 17.4±0.2° and 19.4±0.2° 2θ (°), as determined by using Cu-Kα radiation. XRPD analysis is as shown in FIG. 18.

According to the following experimental examples, the present invention can be better understood. However, those skilled in the art can easily understand that the content described in the experimental examples are only used to illustrate the present invention, and should not and will not limit the present invention described in detail in the claims.

Experimental Example 1 Evaluation of PDE9 by an Enzymatic Method

Test substances: the compound of formula (I) was prepared by example 1 of the present invention, the crystal form I was prepared by example 2 of the present invention, and the crystal form II was prepared by example 16 of the present invention.

1. Experimental Materials and Instruments

PDE9A2 enzyme (BPS, Cat. No. 60090)
384-well plate (Perkin Elmer, Cat. No. 6007279)
IMAP FP PDE Evaluation Kit (a kit for detecting enzyme activity) (Molecular Devices P/N R8175)

2. Test Steps

Preparation of test substances: using the solvent DMSO, the test substances were prepared into a 10 mM stock solution for long-term storage; the stock solution was diluted 100 times with DMSO to obtain a 100 μM working solution of the test substances; and the working solution of the compounds was diluted 3 times with DMSO to obtain a total of 8-10 concentration gradients of a diluted solution of the test substances (100×).

Incubation with treatment: the diluted solution of the test substances was pipetted into a 384-well plate using Echo, a system for pipetting very small amount of liquid; to each test substance well, 200 nL of the diluted solution of the test substances and 10 μL of the PDE9A2 enzyme solution were added, and the plate was centrifuged at 1000 rpm for 1 min, and then incubated at room temperature for 15 min. According to the instructions of the IMAP FP PDE Evaluation Kit (a kit for detecting enzyme activity), 10 μL of a substrate mixed liquor was added, and the mixture was centrifuged at 1000 rpm for 1 min and incubated with shaking at room temperature for 30 min. Finally, a stop solution was added to terminate the reaction system, and the mixture was incubated with shaking at room temperature for 60 min. In the maximum reading well (Max), the compound was replaced with the solvent DMSO; and in the minimum reading well (Min), the test substances and the enzyme solution were replaced with the solvent DMSO.

Detection: a microplate reader was used to detect the fluorescence reading (F) at 480 nm/535 nm.

Calculation: the inhibition rate was calculated according to the following formula, and GraphPad Prism 5.0 was used to fit $IC_{50}$:

$$\text{Inhibition rate (\%)} = \frac{F\text{Max} - F \text{ Compound}}{F\text{Max} - F\text{Min}} \times 100\%$$

3. Experimental Results as Shown in Table 1 Below:

TABLE 1

| Test substances | PDE9 enzyme inhibitory activity PDE9A2 $IC_{50}$ (nM) |
|---|---|
| Compound of formula (I) | 15 |
| Crystal form I | 5 |
| Crystal form II | 11 |

It can be seen from Table 1 that the compound of formula (I), crystal form I and crystal form II of the present invention all have an excellent PDE9 enzymatic inhibitory activity, and have potential application values for treating PDE9-mediated diseases.

Experimental Example 2 Pharmacokinetic Evaluation Experiment of the Compound and Crystal Form I of the Present Invention in Rats Animals: male SD rats Test substances: the compound of formula (I) was prepared by example 1 of the present invention, and the crystal form I was prepared by example 2 of the present invention.

Administration to Animals and Sample Collection:

the compound of formula (I) for the experiment was dissolved with 2% DMSO+10% PEG400+88% (28% HP-β-CD) physiological saline to prepare a solution; the solution of the test substance was administered to SD rats by gavage at a dose of 5.0 mg/kg; and the blood sampling time points were 15 min, 30 min, 1 h, 2 h, 4 h, 6 h, 8 h and 24 h after administration.

The compound of formula (I) for the experiment was dissolved with 2% DMSO+10% PEG400+88% (28% HP-β-CD) physiological saline to prepare a solution; the solution of the test substance was administered to SD rats by intravenous bolus at a dose of 1 mg/kg; and the blood sampling time points were 5 min, 15 min, 30 min, 1 h, 2 h, 4 h, 6 h, 8 h and 24 h after administration.

The crystal form I for the experiment was dissolved with 5% DMSO+10% PEG400+85% (20% captisol) physiological saline solution to prepare a solution; the solution of the test substance was administered to SD rats by gavage at a dose of 60.0 mg/kg; and the blood sampling time points were 15 min, 30 min, 1 h, 2 h, 4 h, 8 h, 24 h, 30 h and 48 h after administration.

The crystal form I for the experiment was dissolved with 2% DMSO+10% PEG400+88% (28% HP-β-CD) physiological saline to prepare a solution; the solution of the test substance was administered to SD rats by intravenous bolus at a dose of 5 mg/kg; and the blood sampling time points were 5 min, 15 min, 30 min, 1 h, 4 h, 8 h, 12 h and 24 h after administration.

Compound of formula (I): the ordinary SD rats were used and fixed; the tails of the rats were heated in a water bath 10 minutes before each time point; and about 100 μL of blood was collected via a tail vein, and then placed in an anticoagulation tube containing $EDTA-K_2$. The blood sample was centrifuged at 8000 rpm at 4° C. for 6 min to obtain a plasma sample, which was prepared within 30 minutes after blood collection. The plasma was stored in a refrigerator at −80° C. before the test.

Crystal form I: the rats were subjected to jugular vein cannulation (JVC); each time, about 0.35 ml of blood was collected from the rats via a jugular vein cannula into a centrifuge tube containing 5 μl of 15% EDTA-K2; the mixture was gently mixed to obtain a homogeneous mixture, and then the centrifuge tube was placed in an ice bath immediately. Within 1 hour after collecting whole blood, the mixture was centrifuged at 4° C. and 2400×g for 5 minutes, and the supernatant was immediately collected to obtain a plasma sample. The plasma was stored in a refrigerator at −80° C. before the test.

Sample Analysis Method:

Compound of Formula (I):

the plasma sample to be tested was taken out from the −80° C. refrigerator, subjected to natural melting at room temperature, and then vortexed for 5 min; 20 L of the plasma sample was precisely pipetted into a 1.5 mL centrifuge tube; 200 L of the internal standard working solution (tolbutamide in methanol) at a concentration of 100 ng/mL was added, and the mixture was mixed homogeneously; the homogeneous mixture was vortexed for 5 min, and then centrifuged at 12000 rpm for 5 min; 50 μL of the supernatant was precisely pipetted into a 96-well plate pre-filled with 150 μL of water/well; and the plate was vortexed for 5 min for homogenization, and subjected to LC-MS/MS assay, with a sample loading volume of 5 μL.

Crystal Form I:

the plasma sample to be tested was taken out from the −80° C. refrigerator, subjected to natural melting at room temperature, and then vortexed for about 30 seconds for homogenization; 50 μl of the sample (50 μl of the blank rat plasma collected for a blank sample and an internal standard blank sample) was pipetted into a 96-well plate (Plate-1); 20 μl of the IS-W solution was added [for the blank sample, 20 μl of methanol was added], and the mixture was mixed homogeneously; 400 μl of acetonitrile was added, and the mixture was vortexed for about 3 minutes with the 96-well plate covered with lid, and centrifuged at 3200×g and 4° C. for 5 minutes. 100 μl of the supernatant was taken and placed into a 96-well plate (Plate-2) and blow-dried with nitrogen flow at 40° C.; 200 μl of reconstituted solution [0.4% formic acid aqueous solution (pH 3.2):acetonitrile (65:35)] was added, and the mixture was vortexed for about 3 minutes with the 96-well plate covered; and LC-MS/MS analysis was performed.

Data Processing Method:

The output results from Analyst 1.6.3 (AB Company) were used as the concentrations of the test substances. Parameters such as mean, standard deviation, and coefficient of variation were calculated by Microsoft Excel (no calculation was required for direct output results from Analyst 1.6.3); and pharmacokinetic parameters were calculated using Pharsight Phoenix 6.1 software NCA ($T_{max}$ was expressed in terms of medians).

Experimental Results:

TABLE 2

Pharmacokinetic experimental results of the compound of formula (I) and crystal form I

| Test substances | Dose iv/PO (mg/kg) | $t_{z1/2}$ iv/PO (h) | $V_{z\_obs}$ iv (L/kg) | $Cl_{obs}$ iv (L/h/kg) | $T_{max}$ PO (h) | $AUC_{last}$ iv/$AUC_{last}$ PO (h*ng/mL) | [$AUC_{last}$ iv/Dose]/ [$AUC_{last}$ PO/Dose] (h*ng/mL) |
|---|---|---|---|---|---|---|---|
| Compound of formula (I) | 1/5 | 1.25/2.68 | 2.13 | 1.45 | 0.5 | 748/1936 | 748/387.2 |
| Crystal form I | 5/60 | 0.453/3.91 | 0.898 | 2.13 | 1.67 | 2447/40067 | 489.4/667.8 |

Notes:
$t_{z1/2}$: terminal elimination half-life;
$Cl_{obs}$: clearance rate;
$V_{z\_obs}$: apparent volume of distribution;
$T_{max}$: time to reach peak plasma concentration;
$AUC_{last}$: area under the plasma concentration-time curve from zero to infinity.

It can be seen from the above table that the compound of formula (I) and crystal form I of the present invention both have excellent pharmacokinetic characteristics.

Experimental Example 3 Stability Test of Crystal Form I of the Present Invention Test substances: the crystal form I was prepared by example 2 of the present invention.

Method: the appropriate amount of crystal form I samples were taken and placed openly at 60° C. and RH 92.5% under light; and the samples were collected on day 5, day 10, and day 30 to investigate changes in the trait, content, and moisture of the samples.

Results:

TABLE 3

Test results of influencing factors

| Placement conditions | Trait | Content (%) | Moisture (%) |
|---|---|---|---|
| 0 day | Yellow powder | 99.7 | 0.08 |
| Placed openly at 60° C. for 5 days | Yellow powder | 99.8 | 0.06 |
| Placed openly at 60° C. for 10 days | Yellow powder | 99.8 | 0.10 |
| Placed openly at 60° C. for 30 days | Yellow powder | 100.1 | 0.12 |
| Placed openly under light for 5 days | Yellow powder | 99.7 | 0.06 |
| Placed openly under light for 10 days | Yellow powder | 99.3 | 0.13 |
| placed openly under light for 30 days | Yellow powder | 100.0 | 0.09 |
| Placed openly at RH 92.5% for 5 days | Yellow powder | 99.7 | 0.04 |
| Placed openly at RH 92.5% for 10 days | Yellow powder | 100.3 | 0.09 |
| Placed openly at RH 92.5% for 30 days | Yellow powder | 100.5 | 0.09 |

Conclusion: after placed for 30 days under conditions of various influencing factors, the crystal form I of the present invention shows no obvious changes in the trait, related substances, content, and moisture, indicating a good stability.

Experimental Example 4 Determination of Solubility of the Compound of the Present Invention in Test Solutions at Different pHs and Water Test substances: the compound of formula (I) was prepared by example 1 of the present invention, the crystal form I was prepared by example 2 of the present invention, the crystal form II was prepared by example 16 of the present invention, the crystal form III was prepared by example 20 of the present invention, the crystal form IV was prepared by example 24 of the present invention, the crystal form V was prepared by example 25 of the present invention, the crystal form VI was prepared by example 27 of the present invention, and the crystal form VII was prepared by example 31 of the present invention.

Preparation of Buffered Salt Solutions at Different pHs:

hydrochloric acid solution at pH 1.0:9 ml of hydrochloric acid was pipetted, and water was added for dilution to 1000 ml; the mixture was mixed homogeneously to obtain a hydrochloric acid solution at pH 1.03. Phosphate buffered solution at pH 4.5:1.56 g of sodium dihydrogen phosphate dihydrate was weighed, and 200 ml of water was added to obtain a phosphate buffered solution at pH 4.50. Phosphate buffered solution at pH 6.8:1.56 g of sodium dihydrogen phosphate dihydrate was weighed, and 200 ml of water was added; and the mixture was adjusted to pH 6.80 with 1 mol/L sodium hydroxide solution.

Experimental Process:

preparation of buffered solutions at different pHs (samples for determining solubility):

50 mg of each test substance was weighed, and 5 ml of the hydrochloric acid solution (pH 1.0) was added; and the mixture was mixed homogeneously with shaking. About 2.5 mg of each test substance was weighed, and 5 ml of the phosphate buffered solution (pH 4.5), 5 ml of the phosphate buffered solution (pH 6.8), and 5 ml of ultrapure water were added, respectively; the mixture was mixed homogeneously with shaking, and then placed in a 37° C. water bath shaker for shaking; the samples were collected at 24 hours and subjected to centrifugation; and the supernatant was taken and directly injected (if the solubility was high, the supernatant was diluted with a 0.1 mol/L hydrochloric acid solution to an appropriate multiple and then injected).

The solubility of the samples was quantitatively calculated according to the single-point external standard method. The experimental results are as shown below:

TABLE 4

Solubility of the compound of formula (I) and different crystal forms in test solutions at different pHs/water

| Test substances | 24-hour solubility in buffers at different pHs/water (mg/ml) pH of buffers | | | |
|---|---|---|---|---|
| | pH 1.0 | pH 4.5 | pH 6.8 | Water |
| Compound of formula (I) | 5.27 | 0.16 | 0.16 | 0.17 |
| Crystal form I | 8.6 | 0.13 | 0.11 | 0.11 |
| Crystal form II | 4.54 | 0.16 | 0.14 | 0.16 |
| Crystal form III | Greater than 10 | 0.15 | 0.12 | 0.23 |
| Crystal form IV | 1.64 | 0.13 | 0.13 | 0.14 |
| Crystal form V | 4.67 | 0.35 | 0.36 | 0.33 |
| Crystal form VI | Greater than 10 | 0.17 | 0.14 | 0.26 |
| Crystal form VII | 7.55 | 0.14 | 0.13 | 0.15 |

Conclusion: the solubility of the compound of formula (I) and different crystal forms increases with the increase of the acidity of the solution, and the solubility thereof is better in the test solution at pH 1.0.

Experimental Example 5 Stability Test of Different Crystal Forms of the Compound of the Present Invention Test substances: the crystal form I was prepared by example 2 of the present invention, the crystal form II was prepared by example 16 of the present invention, the crystal form III was prepared by example 20 of the present invention, the crystal form IV was prepared by example 24 of the present invention, the crystal form V was prepared by example 25 of the present invention, the crystal form VI was prepared by example 27 of the present invention, and the crystal form VII was prepared by example 31 of the present invention.

Method: the appropriate amount of different test substances were taken, and placed at 105° C. for 3 days, and at 60° C. and RH 92.5% under light for 5 days and 10 days, respectively; and the samples were collected on day 0, day 3, day 5 and day 10 to investigate the changes in the trait and content of the samples.

Results:

Table 5 and Table 6 show the results of the trait and content after placement at 105° C. for 3 days. Table 7 and Table 8 show the results of the trait and content after placement at 60° C. and RH 92.5% under light for 5 days. Table 9 and Table 10 show the results of the trait and content after placement at RH 92.5% under light for 10 days.

TABLE 5

Results of the trait of different test substances after placement for 3 days

| | Trait | |
|---|---|---|
| Test substances | 0 day | Placed at 105° C. for 3 days |
| Crystal form II | Yellow powder | Yellow powder |
| Crystal form III | Yellow powder | Yellow powder |
| Crystal form VI | Yellow powder | Yellow powder |

TABLE 6

Results of the content of different test substances after placement for 3 days

| | Content (%) | |
|---|---|---|
| Test substances | 0 day | Placed at 105° C. for 3 days |
| Crystal form II | 99.8 | 99.5 |
| Crystal form III | 99.9 | 99.7 |
| Crystal form VI | 99.9 | 99.7 |

Conclusion: after placed at 105° C. for 3 days, different crystal forms of the present invention show no obvious changes in the trait and content, indicating a good stability.

TABLE 7

Results of the trait of different test substances after placement under conditions of different influencing factors for 5 days

| | Trait | | | |
|---|---|---|---|---|
| Test substances | 0 day | Placed at 60° C. for 5 days | Placed at RH 92.5% for 5 days | Placed under light for 5 days |
| Crystal form I | Yellow powder | Yellow powder | Yellow powder | Yellow powder |
| Crystal form III | Yellow powder | Yellow powder | Yellow powder | Yellow powder |
| Crystal form VI | Yellow powder | Yellow powder | Yellow powder | Yellow powder |
| Crystal form VII | Yellow powder | Yellow powder | Yellow powder | Yellow powder |

TABLE 8

Results of the content of different test substances after placement under conditions of different influencing factors for 5 days

| | Content (%) | | | |
|---|---|---|---|---|
| Test substances | 0 day | Placed at 60° C. for 5 days | Placed at RH 92.5% for 5 days | Placed under light for 5 days |
| Crystal form I | 99.7 | 99.8 | 99.7 | 99.7 |
| Crystal form III | 99.9 | 99.9 | 99.9 | 99.8 |
| Crystal form VI | 99.9 | 99.8 | 99.9 | 99.6 |
| Crystal form VII | 100.0 | 99.9 | 100.0 | 99.6 |

Conclusion: after placed under conditions of different influencing factors for 5 days, different crystal forms of the present invention show no obvious changes in the trait and content, indicating a good stability.

TABLE 9

Results of the trait of different test substances after placement under conditions of different influencing factors for 10 days

| | Trait | | |
|---|---|---|---|
| Test substances | 0 day | Placed at RH 92.5% for 10 days | Placed under light for 10 days |
| Crystal form I | Yellow powder | Yellow powder | Yellow powder |
| Crystal form II | Yellow powder | Yellow powder | Yellow powder |
| Crystal form IV | Yellow powder | Yellow powder | Yellow powder |
| Crystal form V | Yellow powder | Yellow powder | Yellow powder |

TABLE 8

Results of the content of different test substances after placement
under conditions of different influencing factors for 10 days

| Test substances | Content (%) | | |
|---|---|---|---|
| | 0 day | Placed at RH 92.5% for 10 days | Placed under light for 10 days |
| Crystal form I | 99.7 | 100.3 | 99.3 |
| Crystal form II | 99.8 | 99.8 | 99.4 |
| Crystal form IV | 90.9 | 90.8 | 90.9 |
| Crystal form V | 97.3 | 97.4 | 98.1 |

Conclusion: after placed under conditions of different influencing factors for 10 days, different crystal forms of the present invention show no obvious changes in the trait and content, indicating a good stability.

The above descriptions are merely preferred embodiments of the present invention but not intended to limit the present invention, and any modifications, equivalent replacements, improvements, etc. made within the spirit and principle of the present invention should be included within the scope of protection of the present invention.

The invention claimed is:

1. A crystal form I of a compound as shown in formula (I), 6-ethyl-4-(4-methoxy-4-methylpiperidin-1-yl)-2-oxo-1,2-dihydro-1,7-diazanaphthalene-3-carbonitrile, wherein the crystal form has an X-ray powder diffraction pattern comprising characteristic peaks at 7.3±0.2°, 13.6±0.2°, 14.5±0.2°, 18.0±0.2°, 19.1±0.2°, 22.0±0.2° and 23.4±0.2° 2θ, by using Cu-Kα radiation,

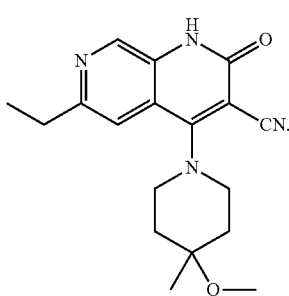

(I)

2. The crystal form I according to claim 1, wherein the X-ray powder diffraction pattern further comprises characteristic peaks at 14.2±0.2°, 16.1±0.2°, 19.4±0.2° and 25.6±0.2° 2θ, by using Cu-Kα radiation.

3. A method for preparing the crystal form I according to claim 1,
wherein the method comprises dissolving the compound of formula (I) in a single or mixed solvent, raising the temperature to reflux until complete dissolution, and slowly decreasing the temperature until the crystal form I is precipitated;
or completely dissolving the compound of formula (I) in a single or mixed solvent, and volatilizing the single or mixed solvent until the system is saturated and the crystal form I is precipitated;
the single or mixed solvent is selected from: one of or a mixture of methanol, ethanol, isopropanol, toluene, acetone, tetrahydrofuran, dichloromethane, dichloroethane, ethyl acetate, acetonitrile, methyl tert-butyl ether, 2-methyltetrahydrofuran, dimethyl sulfoxide and water.

4. The method accordingly to claim 3, wherein the single or mixed solvent is selected from: methanol, ethanol, isopropanol, toluene, acetone, tetrahydrofuran, water\ethanol, water\isopropanol, dichloromethane, ethyl acetate, acetonitrile, dichloromethane \acetone, dichloromethane \acetonitrile, dichloromethane\ethyl acetate, dichloromethane \methyl tert-butyl ether, dichloromethane\tetrahydrofuran, dichloromethane \ethanol, dichloromethane\isopropanol, dichloromethane\toluene, dichloromethane\water\ethanol, and
dichloromethane \water\isopropanol.

5. A crystal form II of a hydrochloride of a compound as shown in formula (I), 6-ethyl-4-(4-methoxy-4-methylpiperidin-1-yl)-2-oxo-1,2-dihydro-1,7-diazanaphthalene-3-carbonitrile, wherein the crystal form has an X-ray powder diffraction pattern comprising characteristic peaks at 4.0±0.2°, 6.7±0.2°, 7.9±0.2°, 13.5±0.2°, 14.2±0.2°, 15.4±0.2°, 20.2±0.2° and 22.0±0.2° 2θ, by using Cu-Kα radiation,

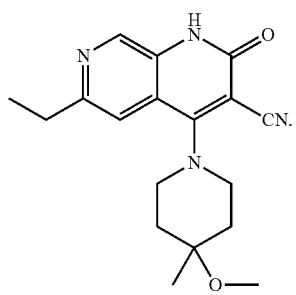

(I)

6. The crystal form II according to claim 5, wherein the X-ray powder diffraction pattern further comprises characteristic peaks at 10.2±0.2°, 13.8±0.2°, 14.6±0.2°, 26.40±0.2° and 26.80±0.2° 2θ, by using Cu-Kα radiation.

7. A method for preparing the crystal form II according to claim 5,
wherein the method comprises adding a single or mixed solvent to the hydrochloric acid of the compound of formula (I), heating the mixture until complete dissolution, and slowly cooling down the heated mixture until the crystal form II is precipitated;
the single or mixed solvent is selected from: one of or a mixture of methanol, ethanol, isopropanol and water.

8. The method according to claim 7, wherein the single or mixed solvent is selected from methanol, ethanol, isopropanol, water\methanol, water\ethanol, and water\isopropanol.

9. A crystal form III of a hydrochloride of a compound as shown in formula (I), 6-ethyl-4-(4-methoxy-4-methylpiperidin-1-yl)-2-oxo-1,2-dihydro-1,7-diazanaphthalene-3-carbonitrile, wherein the crystal form has an X-ray powder diffraction pattern comprising characteristic peaks at 5.2±0.2°, 6.4±0.2°, 15.3±0.2°, 18.6±0.2°, 22.0±0.2° and 26.4±0.2° 2θ, by using Cu-Kα radiation,

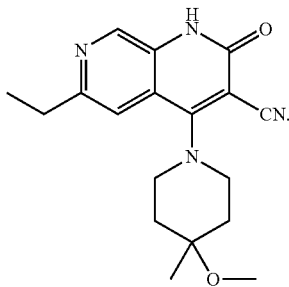

(I)

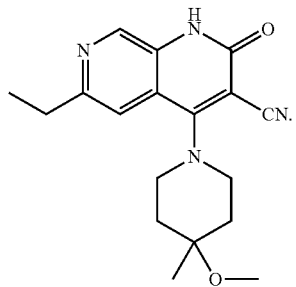

(I)

10. The crystal form III according to claim 9, wherein the X-ray powder diffraction pattern further comprises characteristic peaks at 8.0±0.2°, 10.3±0.2°, 13.5±0.2° and 25.0±0.2° 2θ, by using Cu-Kα radiation.

11. A method for preparing the crystal form III according to claim 9,
wherein the method comprises adding a single or mixed solvent to the hydrochloric acid of the compound of formula (I), heating the mixture until complete dissolution, immediately performing filtration, and concentrating the filtrate until the crystal form III is precipitated; the single or mixed solvent is selected from: one of or a mixture of acetonitrile, acetone, tetrahydrofuran and ethyl acetate.

12. A crystal form IV of a p-toluenesulfonate of a compound as shown in formula (I), 6-ethyl-4-(4-methoxy-4-methylpiperidin-1-yl)-2-oxo-1,2-dihydro-1,7-diazanaphthalene-3-carbonitrile, wherein the crystal form has an X-ray powder diffraction pattern comprising characteristic peaks at 5.8±0.2°, 7.8±0.2°, 9.3±0.2°, 11.3±0.2°, 13.7±0.2°, 14.8±0.2° and 15.7±0.2° 2θ, and further comprising characteristic peaks at 17.1±0.2°, 18.7±0.2°, 20.0±0.2° and 22.4±0.2° 2θ, by using Cu-Kα radiation, 14. A crystal form VI of a sulfate of a compound as shown in formula (I), 6-ethyl-4-(4-methoxy-4-methylpiperidin-1-yl)-2-oxo-1,2-dihydro-1,7-diazanaphthalene-3-carbonitrile, wherein the crystal form has an X-ray powder diffraction pattern comprising characteristic peaks at 4.4±0.2°, 7.1±0.2°, 8.8±0.2°, 14.3±0.2°, 17.8±0.2°, 19.6±0.2° and 21.6±0.2° 2θ, and further comprising characteristic peaks at 25.5±0.2° and 27.7±0.2 2θ, by using Cu-Kα radiation,

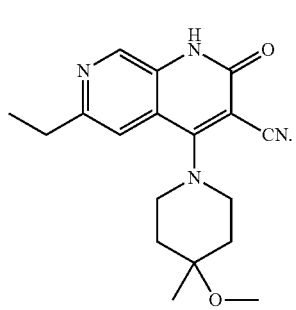

(I)

15. A crystal form VII of a sulfate of a compound as shown in formula (I), 6-ethyl-4-(4-methoxy-4-methylpiperidin-1-yl)-2-oxo-1,2-dihydro-1,7-diazanaphthalene-3-carbonitrile, wherein the crystal form has an X-ray powder diffraction pattern comprising characteristic peaks at 7.1±0.2°, 13.6±0.2°, 14.5±0.2°, 18.0±0.2°, 19.0±0.2°, 22.0±0.2° and 23.4±0.2° 2θ, and further comprising characteristic peaks at 15.0±0.2°, 16.1±0.2°, 17.4±0.2° and 19.4±0.2° 2θ, by using Cu-Kα radiation,

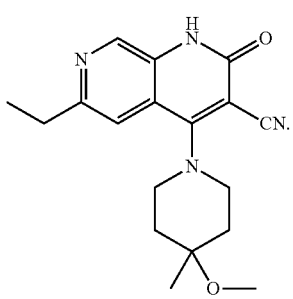

(I)

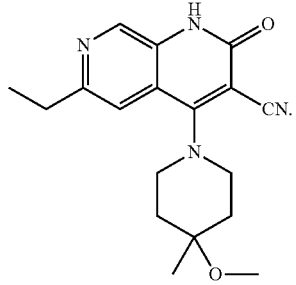

(I)

13. A crystal form V of a methanesulfonate of a compound as shown in formula (I), 6-ethyl-4-(4-methoxy-4-methylpiperidin-1-yl)-2-oxo-1,2-dihydro-1,7-diazanaphthalene-3-carbonitrile, wherein the crystal form has an X-ray powder diffraction pattern comprising characteristic peaks at 7.0±0.2°, 9.7±0.2°, 13.2±0.2°, 18.1±0.2°, 19.5±0.2°, 20.7±0.2° and 21.7±0.2° 2θ, and further comprising characteristic peaks at 16.9±0.2°, 18.6±0.2°, 19.1±0.2°, 20.2±0.2° and 28.0±0.2° 2θ, by using Cu-Kα radiation, 16. A pharmaceutical composition comprising a crystal form selected from the group consisting of crystal form I, crystal form II, crystal form III, crystal form IV, crystal form V, crystal form VI, and crystal form VII, and one or more second therapeutically active agents.

17. A pharmaceutical preparation comprising a crystal form selected from the group consisting of crystal form I, crystal form II, crystal form III, crystal form IV, crystal form V, crystal form VI, and crystal form VII, and one or more pharmaceutical carriers.

18. A method of treating a PDE9-mediated disease, comprising administering to a patient in need thereof a therapeutically effective amount of a crystal form selected from the group consisting of crystal form I, crystal form II, crystal form III, crystal form IV, crystal form V, crystal form VI, and crystal form VII; or of a pharmaceutical composition comprising a crystal form selected from the group consisting of the crystal form I, the crystal form II, the crystal form III, the crystal form IV, the crystal form V, the crystal form VI, and the crystal form VII; or of a pharmaceutical preparation comprising a crystal form selected from the group consisting of the crystal form I, the crystal form II, the crystal form III, the crystal form IV, the crystal form V, the crystal form VI, and the crystal form VII, wherein the PDE9-mediated disease is one of a cognitive disorder, neurodegenerative disorder, heart disease or blood disease, or is metabolic syndrome, obesity, diabetes, hyperglycemia, dyslipidemia, or impaired glucose tolerance.

19. The method of claim 18, wherein the cognitive disorder or neurodegenerative disorder comprises at least one of impairments associated with perception, attention, memory and learning, senile dementia, schizophrenia, age-related memory loss, vascular dementia, stroke, poststroke dementia, post-traumatic dementia, general attention deficit, or attention deficit with learning and memory problems in children, Alzheimer's disease, Lewy body dementia, frontotemporal lobe degeneration dementia, cortical basal ganglionic degeneration dementia, amyotrophic lateral sclerosis disease, Huntington's disease, multiple sclerosis, thalamic degeneration, dementia in Creutzfeldt-Jakob disease, HIV dementia, or depression, the heart disease comprises heart failure; and the blood diseases comprises at least one of anemia, or sickle-cell disease.

* * * * *